US010682147B2

(12) United States Patent
Grant et al.

(10) Patent No.: US 10,682,147 B2
(45) Date of Patent: *Jun. 16, 2020

(54) PATIENT-SPECIFIC TRACKABLE CUTTING GUIDES

(71) Applicant: THE JOHNS HOPKINS UNIVERSITY, Baltimore, MD (US)

(72) Inventors: Gerald Grant, Goshen, KY (US); Peter Liacouras, North Potomac, MD (US); Chad Gordon, Lutherville, MD (US); Ryan Murphy, Columbia, MD (US); Mehran Armand, Fulton, MD (US)

(73) Assignees: The Johns Hopkins University, Baltimore, MD (US); The United States of America, as represented by the Secretary of the Navy, Washington, DC (US); The United States of America, as represented by the Secretary of Defense, Washington, DC (US)

( * ) Notice: Subject to any disclaimer, the term of this patent is extended or adjusted under 35 U.S.C. 154(b) by 515 days.

This patent is subject to a terminal disclaimer.

(21) Appl. No.: 15/100,252

(22) PCT Filed: Nov. 24, 2014

(86) PCT No.: PCT/US2014/067174
§ 371 (c)(1),
(2) Date: May 27, 2016

(87) PCT Pub. No.: WO2015/081027
PCT Pub. Date: Jun. 4, 2015

(65) Prior Publication Data
US 2017/0000498 A1    Jan. 5, 2017

Related U.S. Application Data

(60) Provisional application No. 62/049,866, filed on Sep. 12, 2014, provisional application No. 61/940,196, (Continued)

(51) Int. Cl.
*A61B 17/15* (2006.01)
*G16H 50/50* (2018.01)
(Continued)

(52) U.S. Cl.
CPC .......... *A61B 17/15* (2013.01); *A61B 17/1695* (2013.01); *A61B 17/176* (2013.01);
(Continued)

(58) Field of Classification Search
CPC ..................................................... A61B 17/15
See application file for complete search history.

(56) References Cited

U.S. PATENT DOCUMENTS 3,457,922 A    7/1969 Ray
4,436,684 A    3/1984 White
(Continued)

FOREIGN PATENT DOCUMENTS

CN        101528158 A      9/2009
WO    2012147114 A1      11/2012
(Continued)

OTHER PUBLICATIONS

International Search Report dated Mar. 5, 2015 from corresponding International Application No. PCT/US2014/067174; 4 pgs.
(Continued)

*Primary Examiner* — Zade Coley
(74) *Attorney, Agent, or Firm* — MH2 Technology Law Group LLP

(57) ABSTRACT

A surgical guide assembly having an attachment device configured to be coupled to a bone. A cut location indicator
(Continued)

is coupled to the attachment device. The cut location indicator identifies a location where the bone is to be cut. An arm is coupled to the attachment device, the cut location indicator, or both. A support structure is coupled to the arm. The support structure is configured to have a trackable feature coupled thereto.

10 Claims, 27 Drawing Sheets

Related U.S. Application Data filed on Feb. 14, 2014, provisional application No. 61/910,204, filed on Nov. 29, 2013.

(51) Int. Cl.
| | |
|---|---|
| *A61B 17/17* | (2006.01) |
| *G16H 20/40* | (2018.01) |
| *A61B 34/10* | (2016.01) |
| *A61B 34/20* | (2016.01) |
| *A61B 17/16* | (2006.01) |
| *A61B 17/80* | (2006.01) |
| *A61F 2/28* | (2006.01) |
| *G06F 19/00* | (2018.01) |

(52) U.S. Cl.
CPC ...... *A61B 17/1739* (2013.01); *A61B 17/8085* (2013.01); *A61B 34/10* (2016.02); *A61B 34/20* (2016.02); *A61F 2/2803* (2013.01); *G06F 19/3481* (2013.01); *G16H 20/40* (2018.01); *G16H 50/50* (2018.01); *A61B 2034/105* (2016.02); *A61B 2034/108* (2016.02); *A61B 2034/2051* (2016.02); *A61B 2034/2055* (2016.02); *A61B 2034/2065* (2016.02); *Y02A 90/26* (2018.01)

(56) References Cited

U.S. PATENT DOCUMENTS

| | | | |
|---|---|---|---|
| 5,279,575 A | 1/1994 | Sugarbaker | |
| 5,741,215 A | 4/1998 | DUrso | |
| 5,810,712 A | 9/1998 | Dunn | |
| 6,079,681 A | 6/2000 | Stern et al. | |
| 6,112,109 A | 8/2000 | DUrso | |
| 6,120,290 A | 9/2000 | Fukushima et al. | |
| 6,226,548 B1 | 5/2001 | Foley et al. | |
| 6,254,639 B1 | 7/2001 | Peckitt | |
| 6,285,902 B1 | 9/2001 | Kienzle, III et al. | |
| 6,491,699 B1 | 12/2002 | Henderson et al. | |
| 6,500,179 B1 | 12/2002 | Masini | |
| 6,608,628 B1 | 8/2003 | Ross et al. | |
| 6,726,678 B1 | 4/2004 | Nelson et al. | |
| 6,796,986 B2* | 9/2004 | Duffner | A61B 17/15 606/86 R |
| 6,845,175 B2 | 1/2005 | Kopelman et al. | |
| 6,932,842 B1 | 8/2005 | Litschko et al. | |
| 7,050,877 B2 | 5/2006 | Iseki et al. | |
| 7,113,841 B2 | 9/2006 | Abe et al. | |
| 7,510,557 B1 | 3/2009 | Bonutti | |
| 7,596,399 B2 | 9/2009 | Singhal et al. | |
| 7,747,305 B2 | 6/2010 | Dean et al. | |
| 7,747,318 B2 | 6/2010 | John et al. | |
| 7,792,341 B2 | 9/2010 | Schutyser | |
| 7,857,821 B2 | 12/2010 | Couture et al. | |
| 7,953,260 B2 | 5/2011 | Weinzweig et al. | |
| 8,086,336 B2 | 12/2011 | Christensen | |
| 8,096,997 B2 | 1/2012 | Plaskos et al. | |
| 8,221,430 B2 | 7/2012 | Park et al. | |
| 8,221,461 B2* | 7/2012 | Kuiper | A61F 2/4405 606/247 |
| 8,357,165 B2 | 1/2013 | Grant et al. | |
| 8,397,732 B2 | 3/2013 | Singhal et al. | |
| 8,403,934 B2 | 3/2013 | Angibaud et al. | |
| 8,428,315 B2 | 4/2013 | Suetens et al. | |
| 8,518,085 B2 | 8/2013 | Winslow et al. | |
| 8,535,063 B1 | 9/2013 | Amato | |
| 8,650,005 B2 | 2/2014 | Liao | |
| 8,706,285 B2 | 4/2014 | Narainasamy et al. | |
| 8,781,557 B2 | 7/2014 | Dean et al. | |
| 9,208,558 B2 | 12/2015 | Dean et al. | |
| 9,216,084 B2 | 12/2015 | Gordon et al. | |
| 9,330,206 B2 | 5/2016 | Dean et al. | |
| 9,659,152 B2 | 5/2017 | Mueller | |
| 2001/0021851 A1 | 9/2001 | Eberlein et al. | |
| 2002/0035458 A1 | 3/2002 | Kim et al. | |
| 2002/0165552 A1* | 11/2002 | Duffner | A61B 17/15 606/87 |
| 2004/0091845 A1 | 5/2004 | Azerad et al. | |
| 2004/0172044 A1 | 9/2004 | Grimm et al. | |
| 2004/0204760 A1 | 10/2004 | Fitz et al. | |
| 2005/0043835 A1 | 2/2005 | Christensen | |
| 2005/0113846 A1 | 5/2005 | Carson | |
| 2005/0117696 A1 | 6/2005 | Suzuki et al. | |
| 2006/0142657 A1 | 6/2006 | Quaid et al. | |
| 2006/0195111 A1* | 8/2006 | Couture | A61B 17/15 606/86 R |
| 2007/0167701 A1 | 7/2007 | Sherman | |
| 2007/0207441 A1 | 9/2007 | Lauren | |
| 2007/0225773 A1 | 9/2007 | Shen et al. | |
| 2008/0140149 A1 | 6/2008 | John et al. | |
| 2008/0304725 A1 | 12/2008 | Leitner | |
| 2008/0306490 A1 | 12/2008 | Lakin et al. | |
| 2008/0319448 A1 | 12/2008 | Lavallee et al. | |
| 2009/0088674 A1 | 4/2009 | Caillouette et al. | |
| 2009/0092948 A1 | 4/2009 | Gantes | |
| 2009/0099570 A1 | 4/2009 | Paradis et al. | |
| 2009/0112273 A1 | 4/2009 | Wingeier et al. | |
| 2009/0220122 A1 | 9/2009 | Richards et al. | |
| 2009/0240141 A1 | 9/2009 | Neubauer et al. | |
| 2009/0281623 A1 | 11/2009 | Kast et al. | |
| 2009/0311647 A1 | 12/2009 | Fang et al. | |
| 2010/0145425 A1 | 6/2010 | Jung et al. | |
| 2010/0145898 A1 | 6/2010 | Malfliet et al. | |
| 2010/0261998 A1 | 10/2010 | Stiehl | |
| 2010/0311028 A1 | 12/2010 | Bell et al. | |
| 2011/0029093 A1 | 2/2011 | Bojarski et al. | |
| 2011/0066072 A1 | 3/2011 | Kawoos et al. | |
| 2011/0087465 A1 | 4/2011 | Mahfouz | |
| 2011/0102549 A1 | 5/2011 | Takahashi | |
| 2011/0117530 A1 | 5/2011 | Albocher et al. | |
| 2011/0196377 A1 | 8/2011 | Hodorek et al. | |
| 2011/0208256 A1 | 8/2011 | Zuhars | |
| 2011/0244415 A1 | 10/2011 | Batesole | |
| 2012/0041318 A1 | 2/2012 | Taylor | |
| 2012/0063655 A1 | 3/2012 | Dean et al. | |
| 2012/0109228 A1* | 5/2012 | Boyer | A61B 17/154 606/86 R |
| 2012/0259592 A1 | 10/2012 | Liao | |
| 2013/0035690 A1 | 2/2013 | Mittelstadt et al. | |
| 2013/0122463 A1 | 5/2013 | Csillag | |
| 2013/0204600 A1 | 8/2013 | Mehra | |
| 2013/0211424 A1 | 8/2013 | Thiran et al. | |
| 2013/0211792 A1 | 8/2013 | Kang et al. | |
| 2013/0296872 A1* | 11/2013 | Davison | A61B 17/1739 606/87 |
| 2013/0297265 A1 | 11/2013 | Baloch et al. | |
| 2013/0310963 A1 | 11/2013 | Davison | |
| 2014/0045167 A1 | 2/2014 | Anderson et al. | |
| 2014/0122382 A1 | 5/2014 | Elster et al. | |
| 2014/0329194 A1 | 11/2014 | Sachdeva et al. | |
| 2014/0343557 A1 | 11/2014 | Mueller | |
| 2015/0272691 A1 | 10/2015 | Kim et al. | |
| 2015/0297309 A1 | 10/2015 | Bly et al. | |
| 2015/0328004 A1 | 11/2015 | Mafhouz | |
| 2016/0038243 A1 | 2/2016 | Miller et al. | |
| 2016/0045317 A1 | 2/2016 | Lang et al. | |
| 2016/0346091 A1 | 12/2016 | Bin Abdul Rahman et al. | |
| 2017/0014169 A1 | 1/2017 | Dean et al. | |

(56) References Cited

U.S. PATENT DOCUMENTS

2017/0108930 A1 4/2017 Banerjee et al.
2017/0273797 A1 9/2017 Gordon et al.

FOREIGN PATENT DOCUMENTS

WO 2013101753 A1 7/2013
WO 2014043452 A1 3/2014

OTHER PUBLICATIONS

Murphy et al. "Computer-Assisted, Le Fort-Based, Face—Jaw—Teeth Transplantation: A Pilot Study on System Feasiblity and Translational Assessment." International journal of computer assisted radiology and surgery, 2014.
Bell, R. B., "Computer Planning and Intraoperative Navigation in Orthognathic Surgery"; Journal of Oral and Maxillofacial Surgery; 2011, vol. 69, No. 3, pp. 592-605.
Cevidances, L. et al. Three-dimensional surgical simulation:, American Journal of Orhodontics and Dentofacial Orhopedics, vol. 138, Issue 3, Sep. 2010, pp. 361-371 (Year:2010).
Chapuis et al., "A new approach for 3D computer-assisted orthognathic surgery-first clinical case", Elsevier, International Congress Serier, vol. 1281, May 2005, pp. 1217-1222 (Year: 2005).
Chapuis, J. et al., "A New System for Computer-Aided Preoperative Planning and Intraoperative Navigation During Corrective Jaw Surgery", IEEE, Transactions on Information Technology in Biomedicine, vol. 11, No. 3, May 2007, pp. 274-287 (Year: 2007).
Extended European Search Report dated Jul. 27, 2018 in corresponding EP Application No. 15862375, 8 pages.
Extended European Search Report dated May 24, 2018 in corresponding EP Application No. 15862868, 8 pages.
Goh, R. et al., "Customized fabricated implats after previous failed cranioplasty", Journal of Plastic, Reconstructive and Aesthetic Surgery, vol. 63, 2010, pp. 1479-1484.
Gordon et al.; "Overcoming Cross-Gender Differences and Challenges in Le Fort-Based, Craniomaxillofacial Transplantation With Ehanced Computer-Assisted Technology"; Annals of Plastic Surgery; Oct. 2013, vol. 71, No. 4; pp. 421-428.
International Search Report and Written Opinion in International Application No. PCT/US2015/062521, 12 pages.
International Search Report and Written Opinion dated Mar. 9, 2015 from corresponding International Application No. PCT/US2014/067671; 13 pages.
International Search Report and Written Opinion in International Application No. PCT/US2015/062516,10 pages.
International Search Report and Written Opinion dated Sep. 12, 2016 for PCT/US2016/030447.
International Search Report dated Feb. 24, 2015 from corresponding International Application No. PCT/US2014/067504; 5 pgs.
International Search Report dated Mar. 13, 2015 from corresponding International Application No. PCT/US2014/067167; 5 pgs.
International Search Report dated Mar. 20, 2015 from corresponding International Application No. PCT/US2014/067692; 4 pgs.
International Search Report dated Mar. 5, 2015 from corresponding International Application No. PCT/US2014/067656; 5 pgs.
International Search Reported dated Feb. 24, 2015 from corresponding International Application No. PCT/US2014/067504; 11 pgs.
International Search Reported dated Feb. 27, 2015 from corresponding International Application No. PCT/US2014/067581; 4 pgs.
Jalbert et al., "One-step primary reconstruction for complex craniofocial re section with PEEK custom-made implants", Jounal of Cranio-Maxillo-Facial Surgery, Mar. 2014, vol. 42, No. 2, pp. 141-148.
Lee, M. et al , "Custom implant design for patients with craniel defects", Engineering in Medicine and Biology Magazine, IEEE, 2002, vol. 21, pp. 38-44.
Molla: "General Principles of Bone Grafting in Maxillofacial Surgery"; Jan. 2001; The ORION vol. 8; https://pdfs.semanticsholar.org/ec2e/7ba90a835e873687d9454a848842f26c4.pdf.
Murphy et al., "Computer-assisted single-stage cranioplasty", IN: Engineering in Medicine and Biology Sociaty (EMBC), Aug. 25-29, 2015, pp. 4910-4912.
Schramm et al.; "Non-invasive Registration in Computer Assisted Craniomaxillofacial Surgery"; Rechner-und Sensorgestutzte Chirurgie, 2001, pp. 258-268.
Examination Report in Australian Corresponding Application No. 2015353601 dated Jul. 29, 2019, 4 pages.
Final Office Action in U.S. Appl. No. 15/100,241 dated Aug. 15, 2019, 27 pages.
Notice of Allowance in U.S. Appl. No. 15/100,258 dated Sep. 11, 2019, 6 pages.
Final Office Action in U.S. Appl. No. 15/529,042 dated Sep. 4, 2019, 9 pages.
Examination Report in Australian Corresponding Application No. 2015353523 dated Jun. 28, 2019, 3 pages.
Extended European Search Report in Corresponding EP Application No. 16842453 dated Apr. 16, 2019, 8 pages.
Final Office Action in U.S. Appl. No. 15/100,229 dated Oct. 21, 2019, 48 pages.

\* cited by examiner

| | |
|---|---|
| LIB-PA-ALV | 8° |
| PA-PRN-ALV | 105° |
| PA-PRN-LIB | 89° |
| ALV-PRN-LIB | 16° |
| OCC-PRN | 184 |
| ZY-ZY | 84 |
| PA-PRN | 191 |
| Go-Gn | 62 |
| Go-LIB | 90 |
| PA-ALV | 197 |
| LIB-ALV | 35 |
| Overbite | -10 |
| Overjet | -7 |

| | |
|---|---|
| LIB-PA-ALV | 7° |
| PA-PRN-ALV | 112° |
| PA-PRN-LIB | 84° |
| ALV-PRN-LIB | 28° |
| OCC-PRN | 186 |
| ZY-ZY | 84 |
| PA-PRN | 191 |
| Go-Gn | 62 |
| Go-LIB | 90 |
| PA-ALV | 200 |
| LIB-ALV | 27 |
| Overbite | -2 |
| Overjet | -3 |

DONOR GUIDES

RECIPIENT GUIDES

"HYBRID" RECIPIENT PALATAL SPLINT AND CUSTOM FIXATION PLATE

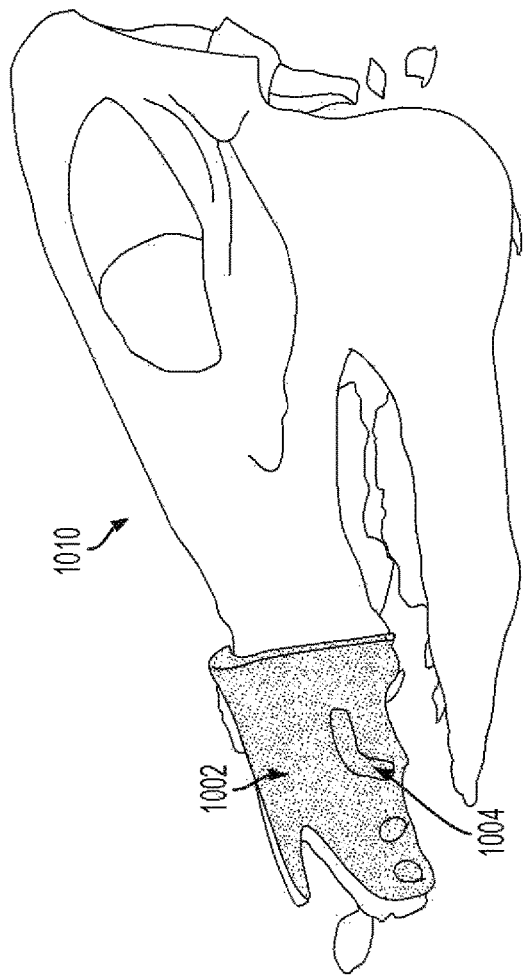
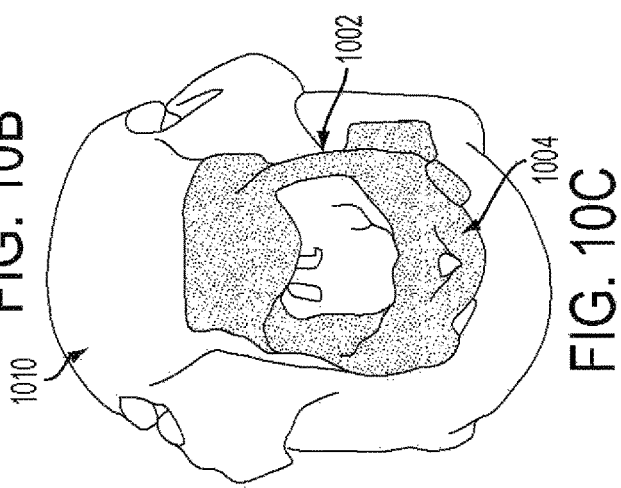
FIG. 10B
FIG. 10C
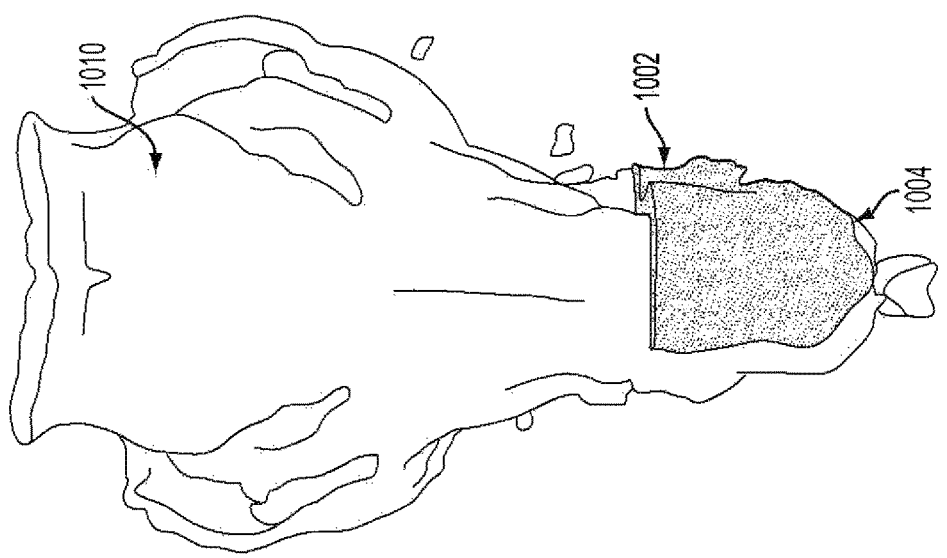
FIG. 10A

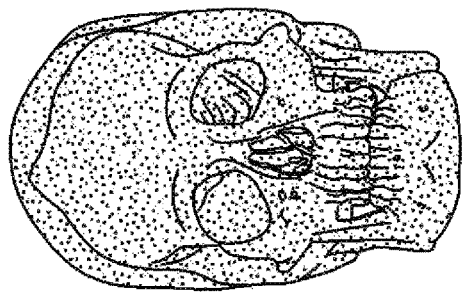
FIG. 12A
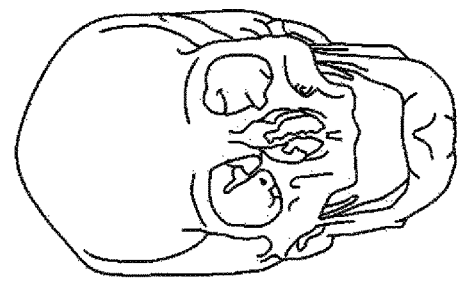
FIG. 12B
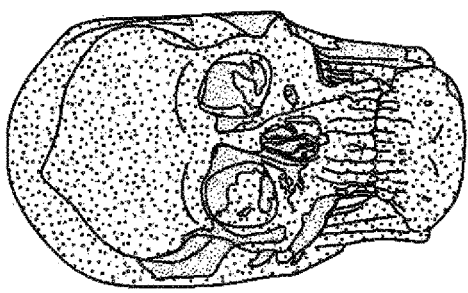
FIG. 12C
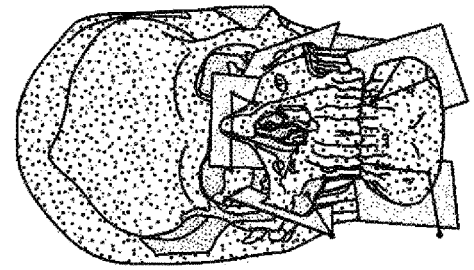
FIG. 12D
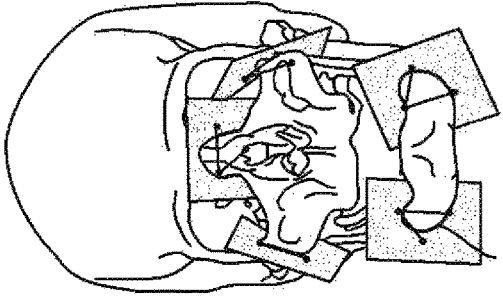
FIG. 12E
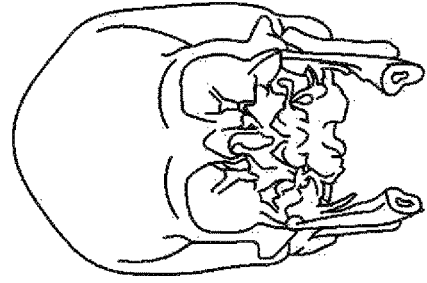
FIG. 12F
FIG. 12G
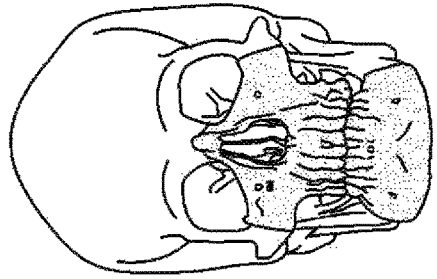
FIG. 12H

PATIENT-SPECIFIC TRACKABLE CUTTING GUIDES

CROSS-REFERENCE TO RELATED APPLICATIONS

This application is a U.S. National Stage application of PCT/US2014/067174 filed 24 Nov. 2014, which claims priority to U.S. Provisional patent application 61/910,204 filed 29 Nov. 2013, U.S. provisional application 61/940,196 filed 14 Feb. 2014, and U.S. provisional application 62/049,866 filed 12 Sep. 2014, the entire disclosures of which are hereby incorporated by reference in their entireties.

GOVERNMENT SUPPORT STATEMENT

This invention was made with government support under Grant Nos. TR000424 and TR001079 awarded by the National Institutes of Health (NIH). The government has certain rights in the invention.

FIELD OF THE INVENTION

This invention relates generally to the field of surgery, particularly craniomaxillofacial surgery, and specifically to the field of computer-assisted craniomaxillofacial surgery and all related orthognathic, neurosurgical and head/face/neck surgical procedures and associated methods, tools, and systems.

BACKGROUND OF THE INVENTION

Facial transplantation represents one of the most complicated scenarios in craniomaxillofacial surgery due to skeletal, aesthetic, and dental discrepancies between donor and recipient. Use of computer technology to improve accuracy and precision of craniomaxillofacial surgical procedures has been described for nearly 30 years, since the increasing availability of computed topography (CT) prompted the development of a CT-based surgical simulation plan for osteotomies.

Two broad approaches to computer-assisted surgery (CAS) have gained popularity: 1) pre-operative computer surgical planning and the use of three-dimensional computer manufactured surgical guides (3D CAD/CAM) to cut and reposition bone and soft tissue, and 2) utilizing intraoperative feedback relative to preoperative imaging for the surgeon to provide more objective data on what is happening beyond the "eyeball test." However, none are meant for real-time placement feedback in areas where guide placement is more challenging, such as the three-dimensional facial skeleton. Also, there are no single platforms built to provide BOTH planning AND navigation—with seemless integration. Additionally, standard off-the-shelf vendor computer-assisted surgery systems may not provide custom features to mitigate problems associated with the increased complexity of this particular procedure. Furthermore, there are currently no validated methods for optimizing outcomes related to facial (e.g., soft tissue), skeletal (e.g., hard tissue), and occlusal (e.g., dental) inconsistencies in the setting of donor-to-recipient anthropometric mismatch—a major hurdle to achieving this specialty's full potential.

One known system includes pre-operative planning and cutting guides by way of computer manufactured stereolithographic models for human facial transplantation. However, such a system uses standard off-the-shelf vendor systems and does not include necessary features to mitigate the increased complexity of this particular procedure.

Additionally, known CAS paradigms for craniomaxillofacial surgery provide little capacity for intraoperative plan updates. This feature becomes especially important since, in some circumstances during the transplantation surgery, it may be necessary to revise and update the preoperative plans intraoperatively.

What is needed in the art, therefore, is a single, fully-integrated platform, providing a computer-assisted surgery solution customized for pre-operative planning, intraoperative navigation, and dynamic, instantaneous feedback—in the form of biomechanical simulation and real-time cephalometrics—for facial transplantation that addresses common shortcomings of existing CAS systems and has the potential to improve outcomes across both the pediatric and adult-based patient population.

SUMMARY

A surgical guide assembly is disclosed. The guide assembly includes an attachment device configured to be coupled to a bone. A cut location indicator is coupled to the attachment device. The cut location indicator identifies a location where the bone is to be cut. An arm is coupled to the attachment device, the cut location indicator, or both. A support structure is coupled to the arm. The support structure is configured to have a trackable feature coupled thereto.

In another embodiment, the surgical guide assembly includes an attachment device having an opening formed therethrough. A screw is configured to be inserted through the opening and at least partially into a bone to couple the attachment device to the bone. A cut location indicator is coupled to the attachment device. The cut location indicator includes a recess or a slot that is aligned with a location where the bone is to be cut. An arm is coupled to the attachment device, the cut location indicator, or both. A support structure is coupled to the arm. A trackable feature is coupled to the support structure.

A method for performing a surgical operation is also disclosed. The method includes coupling a guide assembly to a first bone. The guide assembly includes an attachment device configured to be coupled to first bone. A cut location indicator is coupled to the attachment device. The cut location indicator includes a recess or a slot. An arm is coupled to the attachment device, the cut location indicator, or both. A support structure is coupled to the arm. A trackable feature is coupled to the support structure. The first bone is cut at a location proximate to the cut location indicator. A portion of the first bone is removed after the cutting of the first bone.

Additional advantages of the embodiments will be set forth in part in the description which follows, and in part will be understood from the description, or may be learned by practice of the invention. The advantages will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIGS. 2A-2C provide a schematic overview of a surgical system.

FIG. 5A shows a donor's face-jaw-teeth alloflap in suboptimal position as compared to a recipient's cranium. FIG. 5B shows appropriate face-jaw-teeth positioning with immediate surgeon feedback and updated cephalometric data pertinent to a pre-clinical investigation. A surgeon may adjust the position of face-jaw-teeth segment upwards, downwards, forwards, or backwards based on this real-time cephalometric feedback, as this information helps to predict optimal form and function. For instance, placing the face-jaw-teeth segment forward may improve the patient's airway, but if moved too far forward, it may cause the patient to have a significant overjet (i.e. malocclusion) and abnormal appearance in a profile view.

FIG. 8A illustrates a donor face-jaw-teeth alloflap recovery, FIG. 8B shows a recipient preparation prior to transplant, and FIG. 8C illustrates a custom pre-bent fixation plate and palatal splint designed to achieve face-jaw-teeth alignment and skeletal inset.

FIGS. 10A-10C are a top-view (bird's eye view), a left-sided profile view, and a frontal view, respectively, of images displayed by an imaging system of a surgical system. The images depict a recipient skeleton and include real-time assessment of planned versus actual face-jaw-teeth positions.

FIG. 12 illustrates a virtual osteotomy and planned cut plane placement on virtual representations of a skeletal feature.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

The following embodiments are described for illustrative purposes only with reference to the Figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined with one or more other embodiments to form new embodiments.

Disclosed are embodiments of a computer-assisted surgery system that provides for large animal and human pre-operative planning, intraoperative navigation which includes trackable surgical cutting guides, and dynamic, real-time instantaneous feedback of cephalometric measurements/angles as needed for medical procedures, such as facial transplantation, and many other instances of craniomaxillofacial and orthognathic surgery. Such a system can be referred to as a computer-assisted planning and execution (C.A.P.E.) system and can be exploited in complex craniomaxillofacial surgery like Le Fort-based, face-jaw-teeth transplantation, for example, and any type of orthognathic surgical procedure affecting one's dental alignment, and can include cross-gender facial transplantation.

Figure 1:
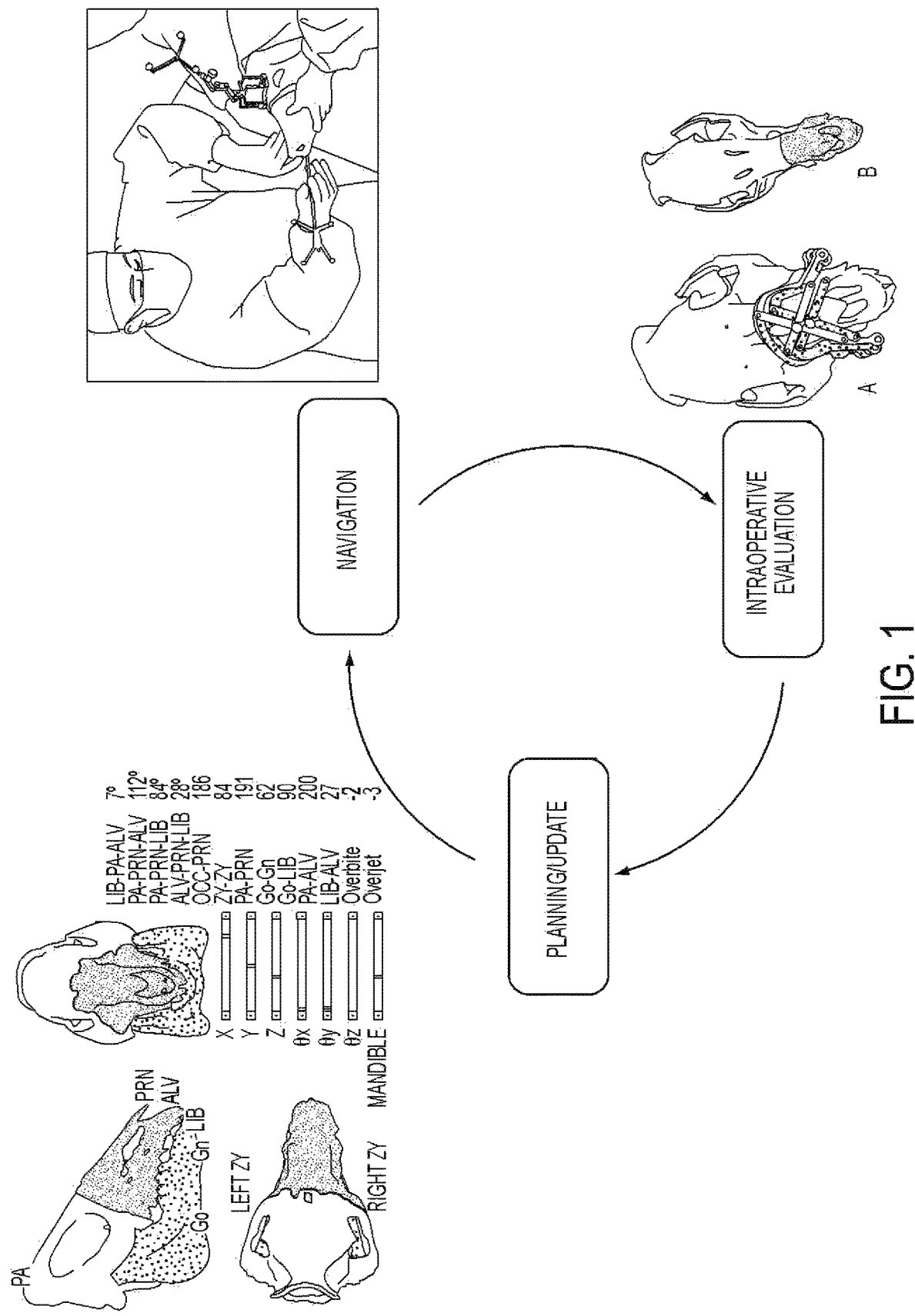
FIG. 1 is a flowchart of a surgical system and method that closes the loop between surgical planning, navigation, and enabling intraoperative updates to a surgical plan.
Figure 2A:
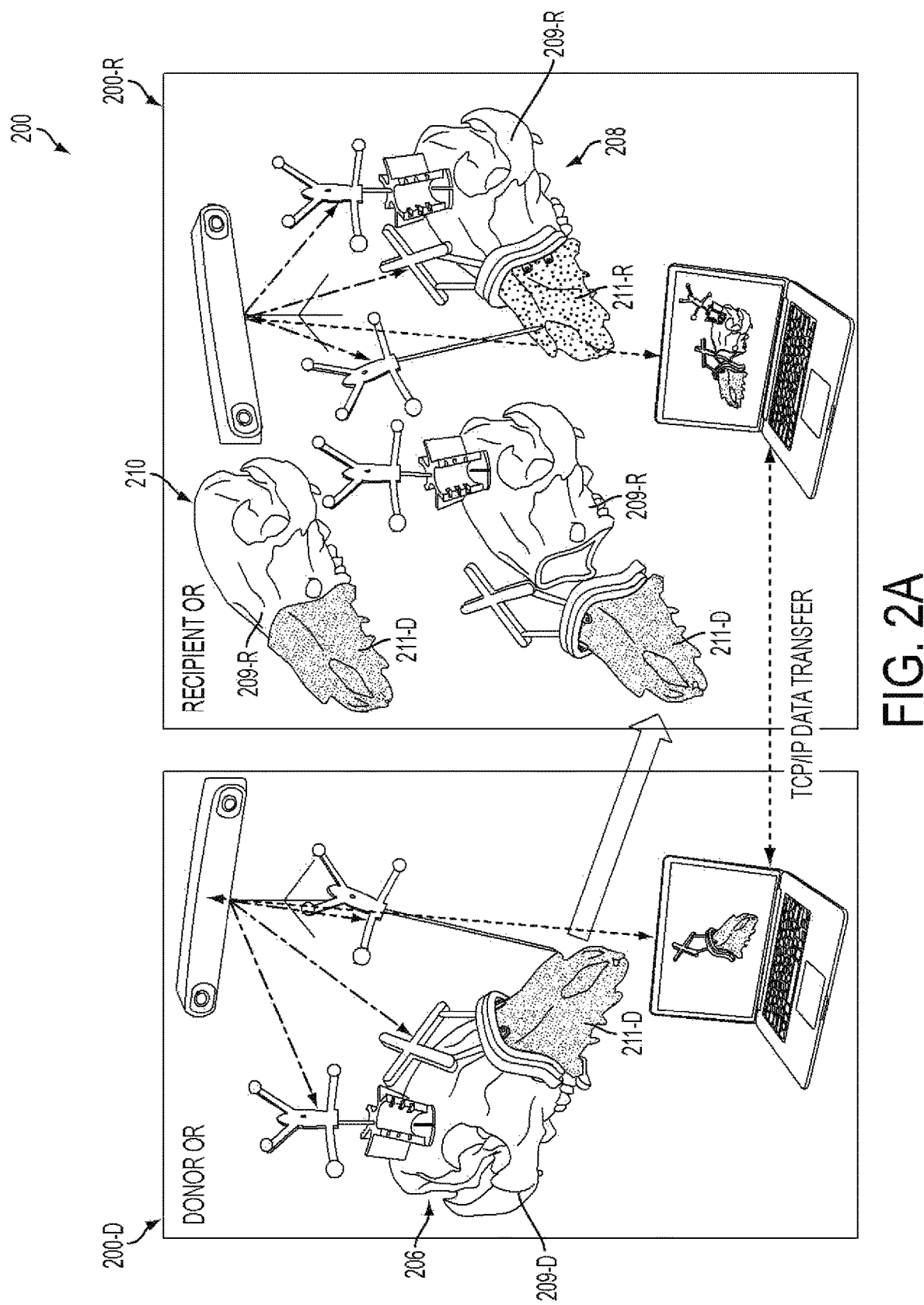
Figure 2B:
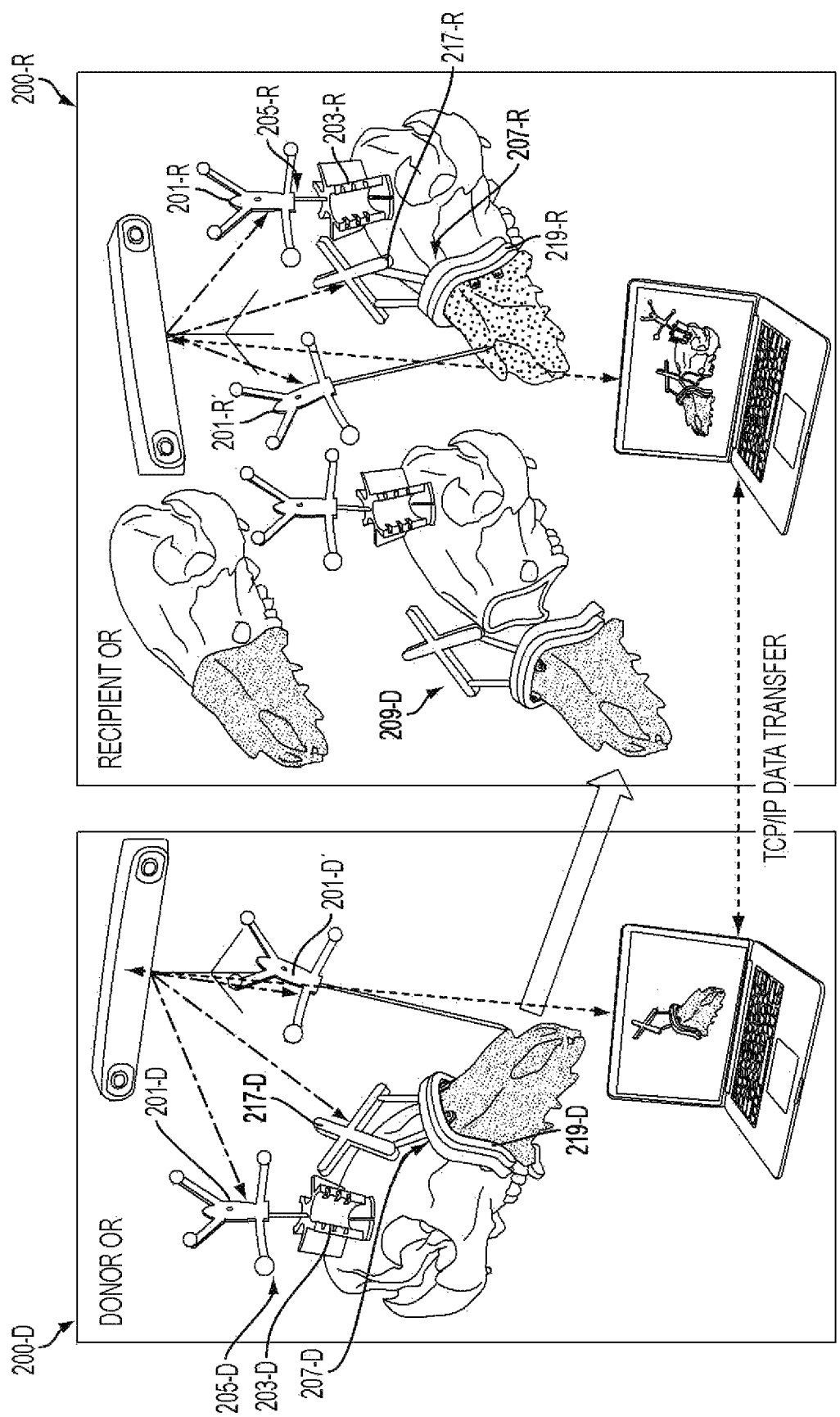
Figure 2G:
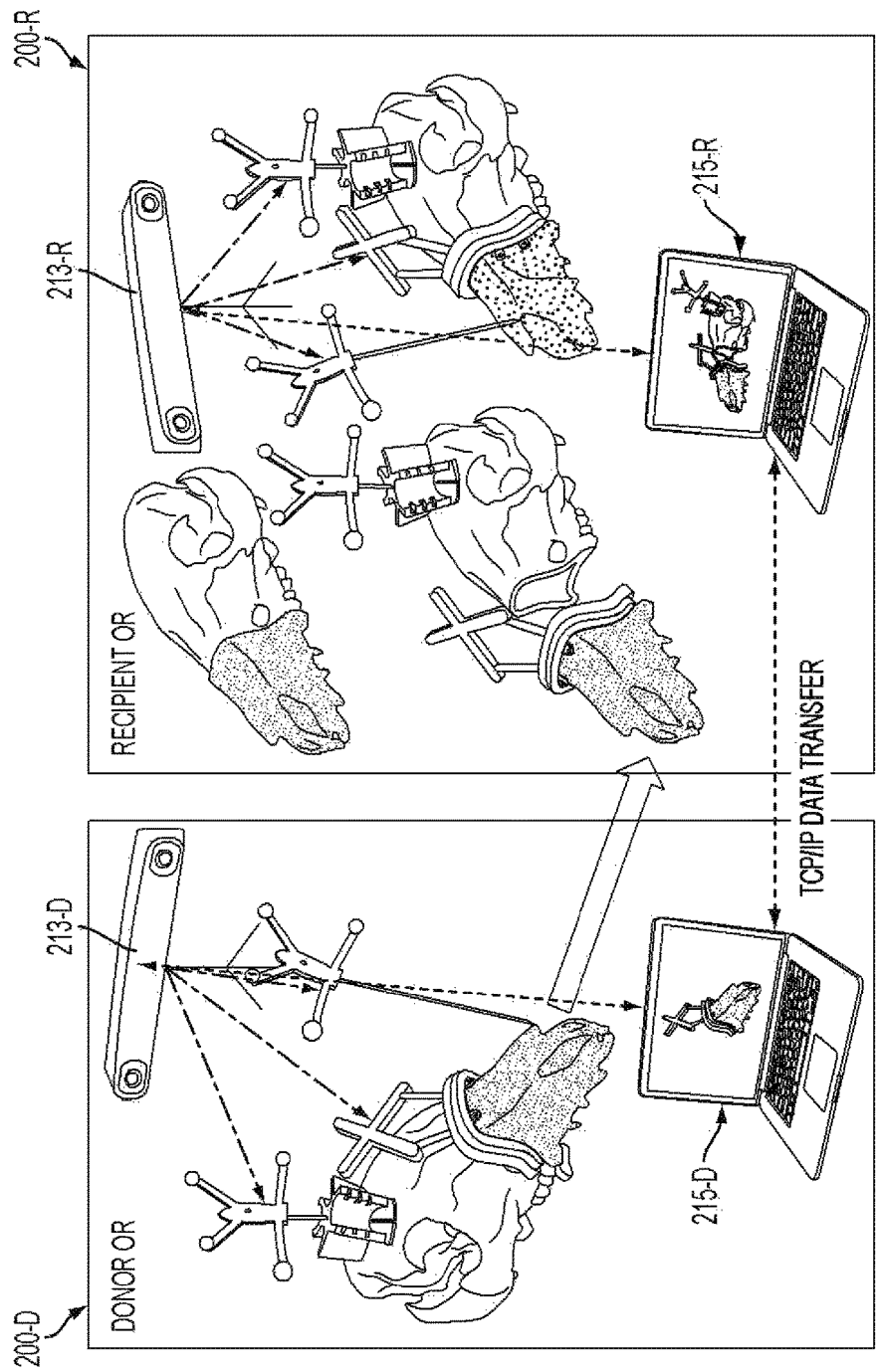
FIGS. 2D-2G are graphical representations of some components and/or features of the surgical system of FIGS. 2A-2C.
Figure 2G:
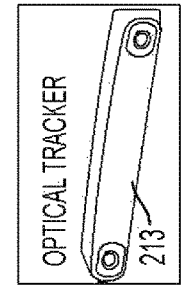
Figure 2F:
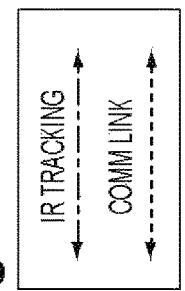
Figure 2E:
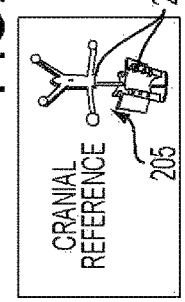
Figure 2D:
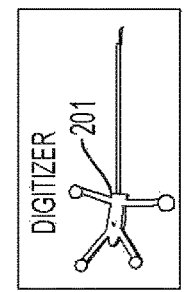

The fundamental paradigm for computer-assisted surgery (CAS) involves developing a surgical plan, registering the plan and instruments with respect to the patient, and carrying out the procedure according to the plan. Embodiments described herein include features for workstation modules within a CAS paradigm. As shown in FIG. 1, a surgical system of the embodiments can enable intraoperative evaluation of a surgical plan and can provide instrumentation for intraoperative plan updates/revisions when needed.

Embodiments can include a system with integrated planning and navigation modules, for example, a system for tracking donor and recipient surgical procedures simultaneously. In general, features of such a system can include: 1) two or more networked workstations concurrently used in planning and navigation of the two simultaneous surgeries for both donor and recipient irrespective of geographic proximity, 2) two or more trackers, such as electromagnetic trackers, optical trackers (e.g., Polaris, NDI Inc.), and the like, for tracking bone fragments, tools, and soft tissues, 3) one or more guides, reference kinematic markers, etc. as required for navigation. These features are described in further detail with respect to FIGS. 2A-2G.

Preoperative planning can include the following tasks: a) segmentation and volumetric reconstruction of the donor and recipient facial anatomy; b) planning for patient-specific cutting guide placement; c) cephalometric analysis and biomechanical simulation of the hybrid skeleton's occlusion and masticatory function, respectively; d) fabrication of the hybrid cutting guides enabling both geometric ("snap-on" fit) and optical navigation; e) 3D mapping the vascular system on both recipient and donor facial anatomy; and f) plan updates, if necessary, based on the feedback from the intraoperative module. As used herein, "snap-on fit" or "snap-on" or "snap on" is used to describe the way an item, such as a cutting guide, attaches to a pre-determined area. That is, the cutting guide actually "snaps-on" to a certain pre-determined area along the facial skeleton, and in all other areas it doesn't fit properly since size and width varies throughout significantly with many convexities and concavities.

Intraoperative tasks of embodiments described herein can generally include: 1) registering the preoperative model reconstructed from the CT data to donor and recipient anatomy; 2) visualizing (e.g., using information from the tracker, such as an electromagnetic tracker, optical tracker, and the like) the instruments and cutting guides to help the surgeon navigate; 3) verifying the placement of cutting guides, and performing real-time cephalometric and biomechanical simulation for occlusion analysis, if, for any reason, the osteotomy sites need to be revised; 4) dynamically tracking the attachment of the donor fragment to the recipient and providing quantitative and qualitative (e.g., visual) feedback to the surgeon for the purpose of improving final outcomes related to form (i.e., overall facial aesthetics) and function (i.e., mastication, occlusion relation, airway patency). Such a procedure is described in further detail below with respect to FIG. 3.

Preoperative Planning

In general, a method for performing a surgery includes a virtual surgical planning step that includes performing segmentation and 3D reconstruction of recipient and donor CT scans (e.g., Mimics 15.01, Materialize, Leuven Belgium). Virtual osteotomies can then be performed within the software to optimize the donor/recipient match. Patient-customized cutting guide templates can then be created (3-matic 7.01, Materialize, Leuven, Belgium). These templates can then be rapid-prototyped via an additive manufacturing modeling process, which can include, but is not limited to, stereolithography or 3D printing and the like. The surgical method and system for performing surgery are described in further detail below.

Figure 4B:
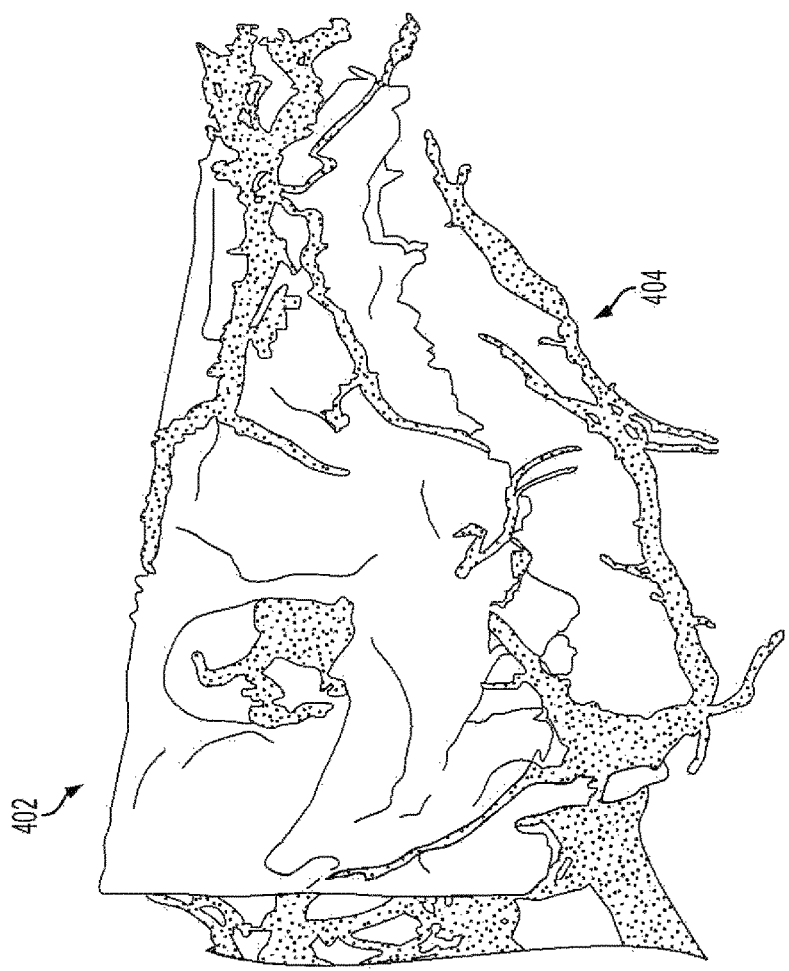
FIG. 4B shows a segmented arterial system of a craniomaxillofacial skeleton generated from CT angiography (CTA) data allowing 3D, intraoperative mapping.
Figure 4A:
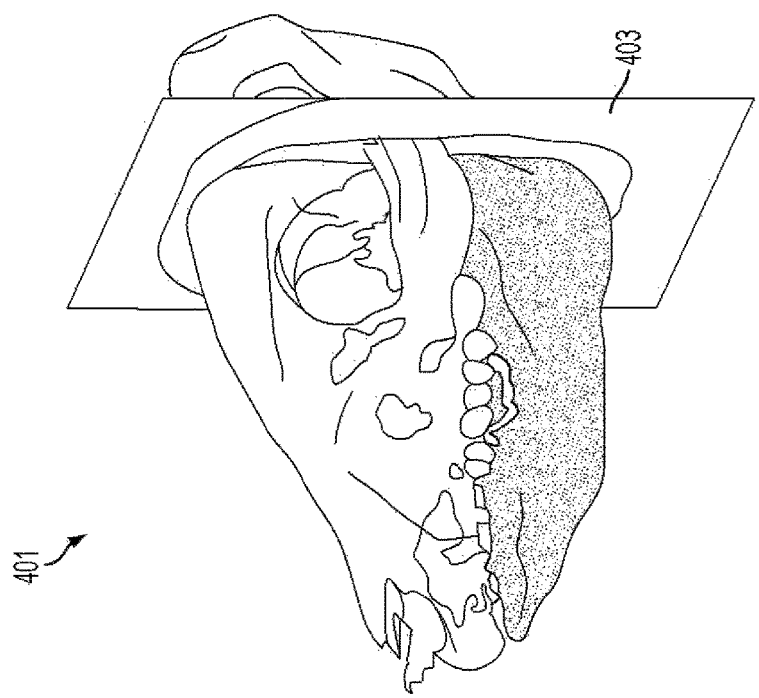
FIG. 4A is a CT-scan of reconstructed images of a size-mismatched facial skeleton generated from segmentation software utilized for pre-operative planning.
Figure 5A:
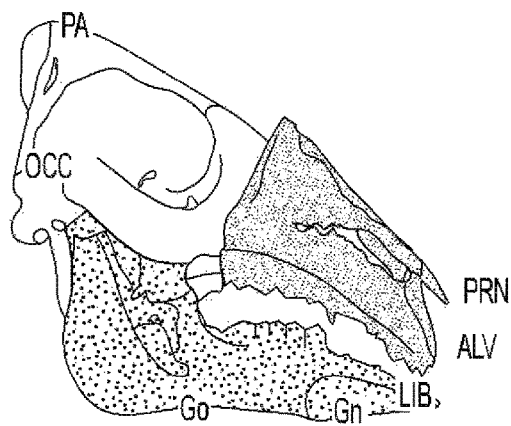
FIGS. 5A-5B show depictions of on-screen images provided by a surgical system, such as the surgical system of FIG. 2A displaying real-time, dynamic cephalometrics and pertinent measurements applicable to humans.
Figure 5A:
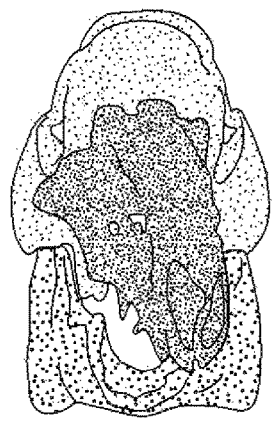
Figure 5A:
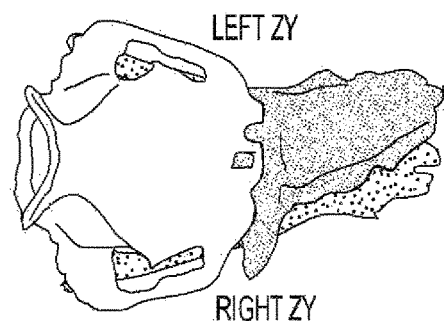
Figure 5B:
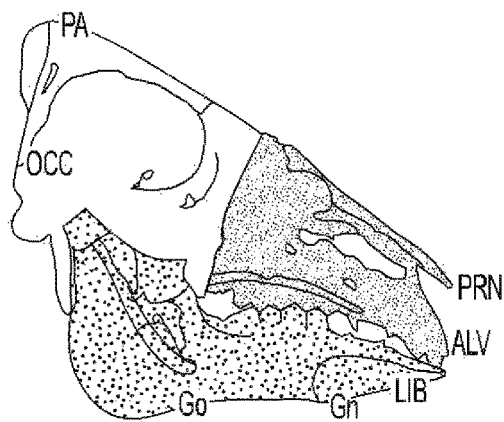
Figure 5B:
Figure 5B:
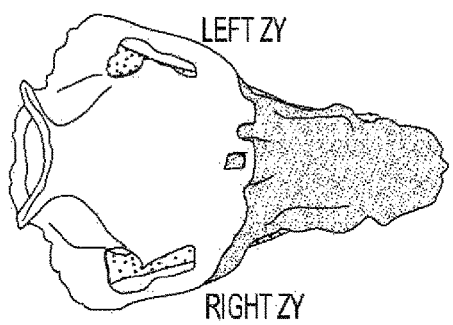

Referring to FIGS. 4A and 4B, during the initial planning stage, surgeons determine a virtual plan 401 based on the recipient's craniomaxillofacial deformity irrespective of the donor. From registered CT data, segmentation software generates volume data for specific key elements (e.g., the mandible, maxilla, and cranium) used for preoperative planning and visualization. The planning workstation automatically generates the expected cut geometry of the donor fragment 402 together with the recipient, thereby defining the predicted facial skeleton with accompanying hybrid occlusion. If available, blood vessels 404 are segmented from CT angiography scans as shown in FIG. 4B. That is, in an embodiment, nerves (via known nerve formations) and vessels (both arteries and veins) can be localized to provide a full anatomical "road map" to the surgeons for a more precise, time-saving anatomical dissection with perhaps decreased blood loss and smaller incisions. The planning module can also perform static cephalometric analysis and evaluation of face-jaw-teeth harmony via biomechanical simulation on varying constructions of the hybrid donor and recipient jaws, such as that shown in FIGS. 5A-5B. Using this tool, the surgeon can evaluate different placements for the donor's face-jaw-teeth alloflap on the recipient's facial skeleton in relation to orbital volumes, airway patency, facial projection, and dental alignment. An automated cephalometric computation for the hybrid face indicates the validity of the planned surgery from both an aesthetic, functional, and reconstructive standpoint based on various measurements of pertinent landmarks as shown, for example, in Tables 1A-B.

TABLE 1A

Pertinent landmarks for cephalometric analysis

| SYMBOL | NAME and DEFINITION |
|---|---|
| Go | Gonion: a point mid-way between points defining angles of the mandible |
| Gn | Gnathion: most convex point located at the symphysis of the mandible |
| ALV | Alveolare: mid-line of alveolar process of the upper jaw, at incisor - alveolar junction |
| LIB | Lower Incisor Base: midline of anterior border of alveolar process of mandible at the incisor-alveolar junction |
| PA | Parietale: most superior aspect of skull in the midline, (formed by nuchal crest of occipital bone and parietal bone) |
| PRN | Pronasale: bony landmark representing anterior limit of nasal bone |
| ZY | Zygion: most lateral point of malar bone |
| OCC | Occipital region: midpoint between the occipital condyles |

TABLE 1B

Cephalometric measurements and related units.

| | | | | | | | | | | | | |
|---|---|---|---|---|---|---|---|---|---|---|---|---|
| | | | | | | | | | | | | |
| | | | | | | | | | LIB- | PA- | PA- | ALV- |
| ZY- | PA- | Go- | Go- | PA- | LIB- | | | OCC- | PA- | PRN- | PRN- | PRN- |
| ZY | PRN | Gn | LIB | ALV | ALV | Overbite | Overjet | PRN | ALV | ALV | LIB | LIB |
| Units mm | mm | mm | Mm | mm | mm | mm | mm | mm | deg | deg | deg | deg |

To evaluate and predict cephalometric relationships both during planning and intra-operative environments, the system can use validated, translational landmarks between swine and human to thereby allow effective pre-clinical investigation. The cephalometric parameters defined by these landmarks can be automatically recalculated as the surgeon relocates the bone fragments using a workstation's graphical user interface.

Figure 6:
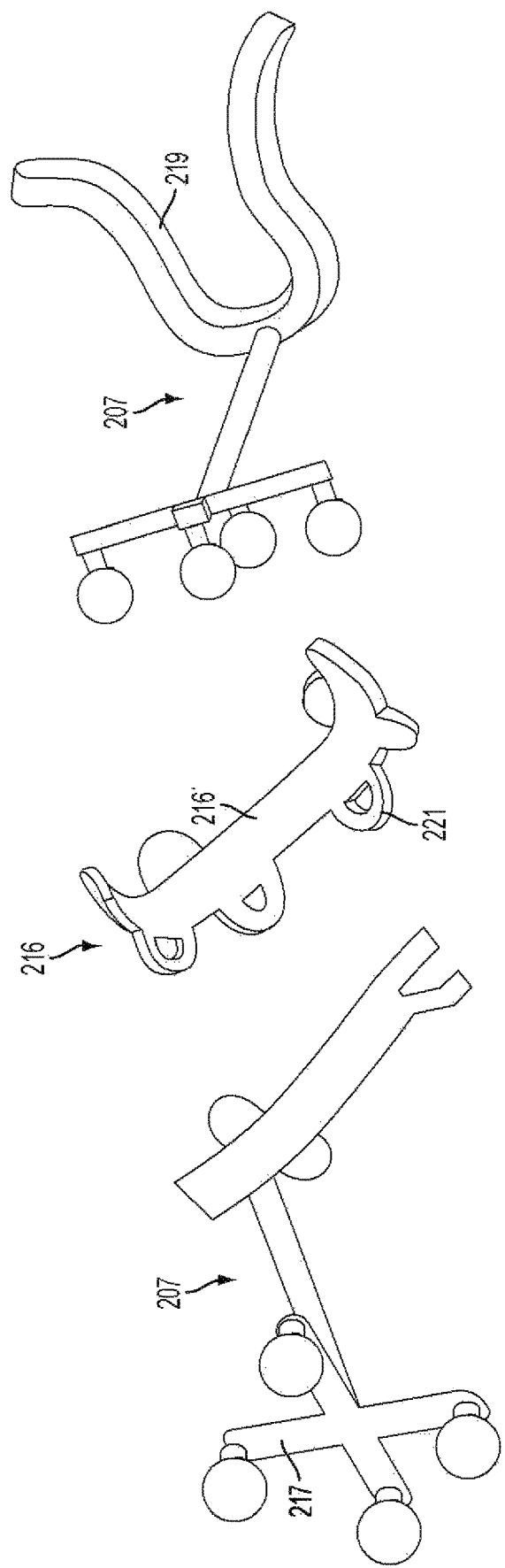
FIG. 6 shows some pre-bent fixation plates with screw holes designed virtually to accommodate the donor-to-recipient skeletal mismatch areas and matching navigational cutting guides of a surgical system, for example, the surgical system of FIGS. 2A-2C.
Figure 8A:
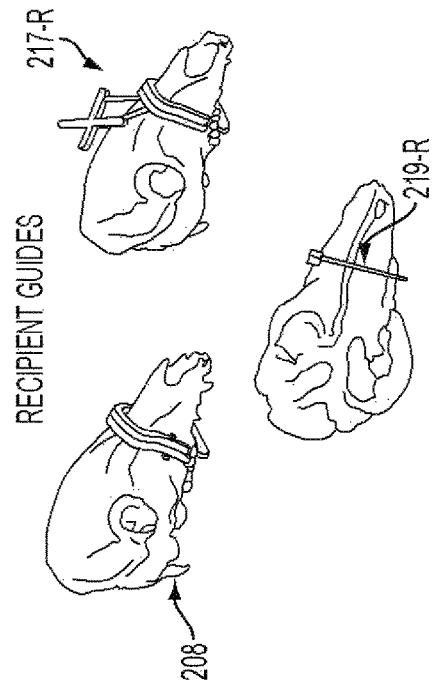
FIGS. 8A-8C are illustrations of cutting guides of the embodiments with navigational capabilities.
Figure 8B:
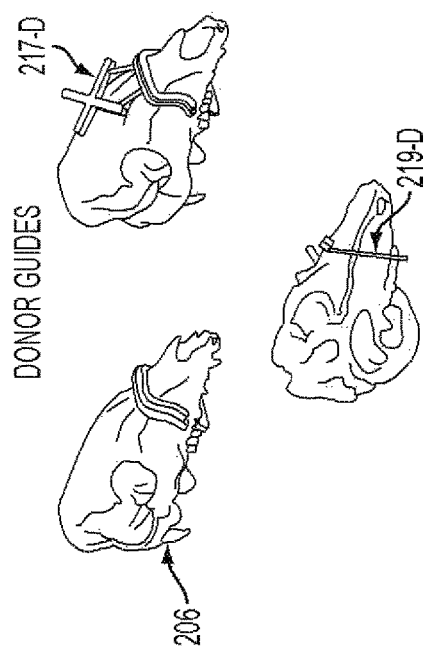
Figure 8C:
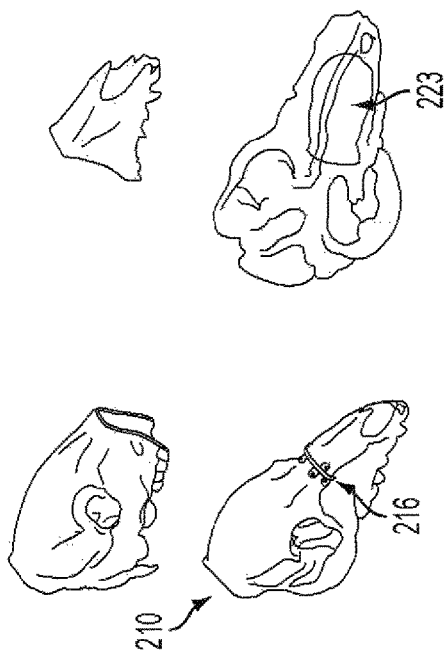

Preoperative planning can also involve fabrication of custom guides 207 (as shown in FIG. 6) and palatal splints 223 (as shown in FIG. 8C). Planned cut planes 403 (as shown in FIG. 4) can be used for defining the geometry of the cutting guides to thereby provide patient-specific cutting guides. These cutting guides can be designed according to the skeletal features through which the cutting plane intersects, such as an outer skeletal surface of a cross section defined by the cutting plane, and can be fabricated via stereolithography, or via any additive manufacture technology. In an embodiment, custom cutting guide templates can be separately designed and navigational registration elements can be added (Freeform Plus, 3D Systems, Rock Hill, S.C.). As discussed above, the surgical guides can be manufactured via additive manufacturing technology (AMT). The cutting guides can, therefore, be a 3D printing material such as a polymer, and can include an attachment surface 216 configured for attaching to a skeletal feature, and can have a "snap-on" fit to both donor and recipient. As described above, the attachment surface may include a contoured surface that corresponds to the contours of the skeletal feature within the planned cut planes. A navigation surface, such as a reference geometry 217 connected, built into, or attached to the guide structure directly or via attachment guides (not shown), enables dynamic intraoperative tracking of guides with respect to the patient's skeleton. Palatal splints ensure planned dento-skeletal alignment fixation following Le Fort-type facial transplants or any similar type of surgery. Fixation plates 216 can include a primary surface 216' and a plurality of fixation surfaces 221, such as eyelets, for screw placement to provide rigid immobilization at the irregular skeletal contour areas along various donor-to-recipient interfaces. Having pre-bent fixation plates decreases total operative times and helps to confirm accurate skeletal alignment by overcoming step-off deformities at bone-to-bone interfaces. Accordingly, at least one of the plurality of fixation surfaces can be located on one side of the primary surface and configured for attaching the fixation surface to a donor skeleton fragment, and at least one of another of the plurality of fixation surfaces is located on another side of the primary surface and configured for attaching the fixation surface to a recipient skeleton. The whole fixation plate or just portions of the fixation plate, such as the primary surface or fixation surfaces can be manufactured via additive manufacturing technology.

The cutting guide's navigation surface can include trackable objects, for example, on the reference geometry, such as infrared (IR) reflective coatings or IR emitters. For example, the trackable objects can include a plurality of integrated tracking spheres, each of which has an IR reflection surfaces.

Intraoperative Surgical Assistance

Figure 7B:
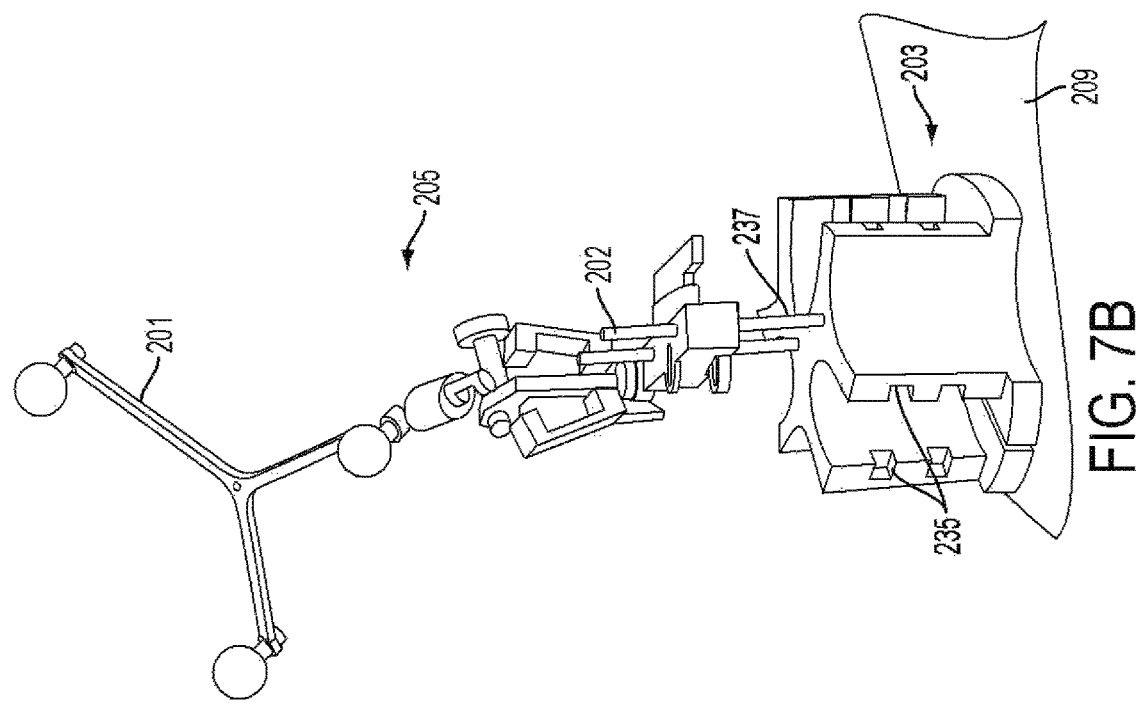
FIG. 7B schematically depicts a detachable rigid body with reflective markers attached to the reference body
Figure 7A:
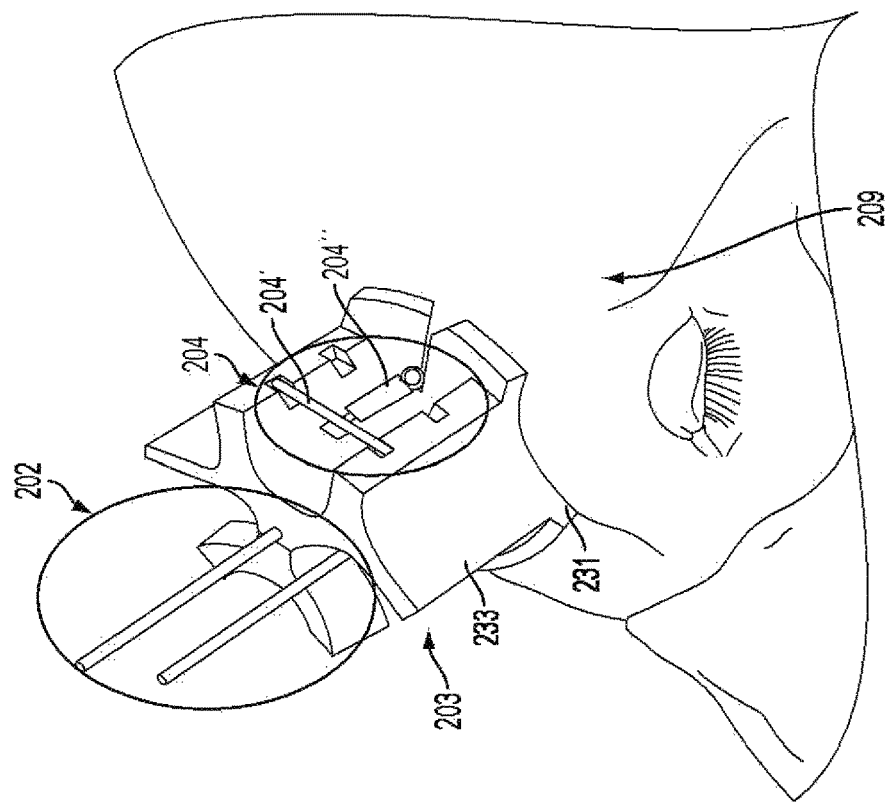
FIG. 7A schematically depicts a kinematic reference mount of an embodiment as it is affixed onto a donor's cranium with intermaxillary screws. A permanent suture (not visible) attaches stabilizers, such as springs and/or cross bars, which allow easy removal and replacement during surgery.

Individual navigation for both donor and recipient surgeries tracks the cutting guides with respect to planned positions. Surgeons can attach a reference unit, such as a kinematic reference mount to three intramedullary fixation (IMF) screws arranged in a triangular pattern on each the donor and recipient craniums as shown in FIG. 7A-7B. Accordingly, in an embodiment, there is a reference unit 205 for providing real-time surgical navigation assistance. The reference unit for providing real-time surgical navigation assistance can include a kinematic mount 203, at least one fixation rod 202, at least one support 204, and reference geometry 201. The kinematic mount 203 can include a base with a plurality of recesses defined by sidewalls 233, at least one pair of slots 235 defined by portions of the sidewalls, with each slot of the pair formed across the recess from the other slot, and at least one guide hole 237 extending through a length of the fixation plate. The at least one fixation rod 202 can extend through the at least one guide hole 237. An end of the at least one support rod can be configured for attaching to a skeleton of a being 209. The at least one support can be disposed in the pair of slots and can be configured to attach to the being. The reference geometry 201 can be attached to the at least one fixation rod.

The at least one support 204 can include at least one cross-bar 204' with ends that are configured for placement in the slots 235, and a spring 204" attached at one end to the at least one cross-bar 204' and attached at another end to the patient (e.g., a human-being). The spring attached at another end to the being can be attached via a suture (further described below). The reference unit 205 can further include a trackable object disposed on the reference geometry. The trackable object disposed on the reference geometry can include an IR reflective surface. The mount 203 can be made via additive manufacturing techniques and can therefore include a polymer. The at least one fixation rod can include a plurality of intramedullary fixation screws. The base can be configured for being detachably mounted on the skeleton of the being 209. The intramedullary fixation screws can be arranged in a triangular pattern. Accordingly the guide-holes can be configured in a triangular pattern on the base.

Accordingly, the mount design permits flexibility in the placement of the IMF screws so that no template is necessary. A spring 204" can attach to each IMF screw via suture threaded through, for example, the eyelets. These springs hold the cranial mount 203 in place and allow easy removal and replacement of the cranial mount (e.g. during positional changes required for bone cuts and soft tissue dissections). This may provide detachability and use of Intramaxillary fixation (IMF) screws for stable attachment.

The reference geometry 201 (e.g., which can be purchased from Brainlab, Westchester, Ill., USA) attached to the kinematic mount 203 provides a static coordinate frame attached to the patient. The surgeon can digitize three bony landmarks (e.g., the inferior aspect of the orbits and antero-superior maxilla) to define a rough registration between the environment and virtual models. For example, three, consistent points can be selected which can be quick to find, easy to reproduce on numerous occasions, and would remain constant irrespective of the user and his/her experience with the systems of the embodiments. The surgeon can thereby collect several point sets from exposed bone using a digitization tool and uses an iterative closest point registration technique to refine the registration. As shown in FIG. 8, once registered, the surgeon navigates the placement of the cutting guide 217 using the combination of "snap-on" geometric design and the tracking system coupled to visual feedback. This allows assessment of inaccuracies related to soft tissue interference, iatrogenic malpositioning, anatomical changes since acquiring original CT scan data, and/or imperfections in cutting guide design or additive manufacturing process.

Self-drilling screws affix the cutting guide to the patient's skeleton to ensure osteotomies are performed along predefined planes, maximizing bony congruity. After dissecting the donor's maxillofacial fragment and preparing the recipient's anatomy, the surgical team transfers the facial alloflap. The system is configured to track the final three-dimensional placement of, for example, the Le Fort-based alloflap providing real-time visualization such as that shown in FIG. 5A-5B. This provides real-time visualization of important structures such as new orbital volumes (vertical limit of inset), airway patency (posterior horizontal limit of inset), and facial projection (anterior horizontal limit of inset). Once confirmed, the surgeon fixates the donor alloflap to the recipient following conventional techniques with plates and screws.

Accordingly, returning to FIGS. 2A-2G, there is a system 2000 for tracking donor and recipient surgical procedures simultaneously. The system can include a donor sub-system 200-D, a recipient sub-system 200-R and a communications link (indicated by the horizontal dotted-line) such as a communication link that provides TCP/IP data transfer between the donor and recipient sub-systems. The donor sub-system can include a first computer workstation 215-D, a first cranial reference module 205-D, a first cutting guide 207-D for attaching to a preselected location of a donor skeleton 206, a first fragment reference module 201-D', and a first tracker 213-D. The first cutting guide 207-D can include an attachment surface 219-R configured for attaching to a skeletal feature, and a navigation surface 217-D connected to the attachment surface and comprising a trackable reference geometry. The first tracker 213-D may be configured to be in communication with the first computer workstation, for example, via a communications link. The first tracker can be configured to track, for example via IR optical tracking, a location of a portion of the first cranial reference module, a portion of the first cutting guide and a portion of the first fragment reference module. The recipient sub-system 200-R can include a second computer workstation 215-R, a second cranial reference module 205-R, and a second tracker 213-R. The second tracker 213-R can be configured to be in communication with the second computer workstation, for example, via a communications link. The second tracker can be configured to track, for example, via IR optical tracking, a location of a portion of the second cranial reference module. The communications link can connect the first computer workstation and the second computer workstation such that the first computer workstation and second computer workstation are able to communicate.

The recipient sub-system 200-R can further include a second fragment reference unit 201-R. The second tracker 213-R can be further configured to track a location of a portion of the second fragment unit.

The recipient sub-system 200-R can further include a second cutting guide 219-R for attaching to a preselected location of a recipient skeleton 208. The second tracker 213-R can be further configured to track a location of a portion of the second cutting guide.

Additionally, when a surgeon has removed the donor skeletal fragment from the donor, it can then be transferred for attachment onto the recipient. Accordingly, the second tracker 213-R can be further configured to track a location of a portion of the first cutting guide 207-D so that it can be matched relative a position of the second cranial reference module 205-R.

The first cranial reference unit, the second cranial reference unit, or both the first and second cranial reference units can include a kinematic mount 205 as described above.

Figure 3:
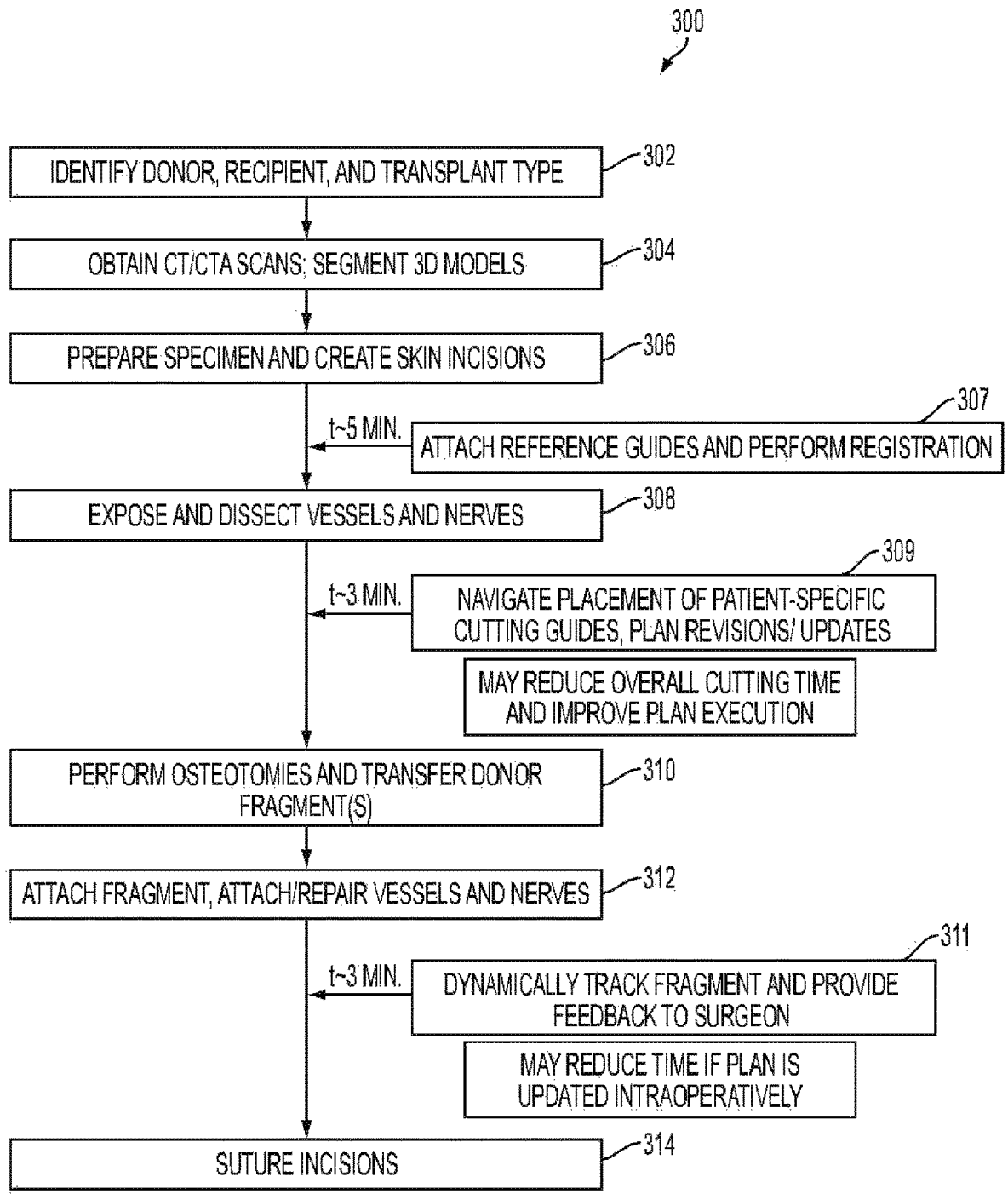
FIG. 3 is a flow chart depicting a procedure associated with use of the surgical system, for example, the surgical system of FIGS. 2A-2C.

Using the system of FIGS. 2A-2G, it is possible to execute a surgical method, such as the surgical method described in FIG. 3. For example, in step 302 a donor, recipient and transplant type are identified. CT/CTA scans of both the donor and recipient are collected and 3D models are created in step 304. The donor and recipients are prepared for surgery with the creation of skin incisions in step 306. The method continues at 307 with attachment of reference guides and performing registration. For example, a first cranial reference unit can be attached to a donor skeleton, a first fragment reference unit can also be attached to the donor skeleton at a location that is different that of the first cranial reference unit. The locations of the first cranial reference unit and the first fragment reference unit can be tracked with a first tracker. 3D reconstructions of the donor skeleton can be constructed showing a first virtual cranial reference unit and first virtual fragment reference unit superimposed on the first 3D reconstruction at locations that correspond to relative positions of the first cranial reference unit and the first fragment reference unit.

A second cranial reference unit can be attached to a recipient skeleton. A second location of the second cranial reference unit can be tracked with a second tracker. A second 3D reconstruction of the recipient skeleton can be created with a second virtual cranial reference unit superimposed on the second 3D reconstruction at a location that corresponds to a location of the second cranial reference unit. At 308, vessels and nerves are dissected and exposed. At this stage, navigation of the patient-specific cutting guides can occur, with plan revision and updates provided periodically. For example, a first cutting guide, such as a patient-specific cutting guide according to the descriptions provided above, can be attached onto the donor skeleton at a preselected location such as that corresponding to a planned cut-plane. The location of the first cutting guide can be tracked with the first tracker. A first virtual cutting guide can be superimposed on the first 3D reconstruction at a location that corresponds to a location of the first cutting guide relative to the location of the first cranial reference unit or the location of the first fragment reference unit.

A first virtual fragment can be formed by segmenting the 3D reconstruction of the donor skeleton at a location adjacent to the first virtual cutting guide. The first virtual fragment can be superimposed on the second 3D reconstruction of the recipient skeleton.

At step 310, a surgeon can perform an osteotomy on the donor skeleton to remove the first fragment but cutting the skeleton along a cutting path defined by the first cutting guide. Upon transferring the removed skeletal fragment from the donor, the first cutting guide can be tracked, by the second tracker, for example, when the fragment is brought near the recipient for attachment. The surgeon can then navigate placement of the cutting guide as it is dynamically tracked at step 311, and will receive feedback from the system such as by referring to a first virtual fragment that is superimposed on the second 3D reconstruction to form a hybrid 3D reconstruction. At step 312, the first fragment can then be attached to the recipient skeleton via known surgical methods and the incisions can be sutured in step 314.

The step of superimposing the first virtual fragment on the second 3D reconstruction of the recipient skeleton can include performing an automated cephalometric computation for the hybrid reconstruction. In fact, the step of superimposing the first virtual fragment on the second 3D reconstruction can include providing a communications link between a first workstation on which the first 3D reconstruction is displayed and a second workstation on which the second 3D reconstruction is displayed, and initiating a data transfer protocol that causes the first workstation and the second workstation to send electronic signals through the communications link.

Surgical methods of the embodiments described above can also include attaching a second cutting guide at a preselected location on the recipient skeleton. The second cutting guide can also include features of the cutting guide described above.

For the surgical methods of embodiments described herein the donor skeleton can include a male skeleton or a female skeleton and the recipient skeleton can include a female skeleton. Alternatively, the donor skeleton can include a male or female skeleton and the recipient skeleton can include a male skeleton.

Surgical methods of the embodiments can further include steps for assessing a size-mismatch between the donor skeleton and the recipient skeleton by measuring a dorsal maxillary interface between the first fragment and recipient skeleton. In an embodiment, the surgical method can include selecting a location of the first fragment onto the recipient skeleton that minimizes dorsal step-off deformity at the area of osteosynthesis. In an embodiment, the first cutting guide, the second cutting guide, or both the first cutting guide and the second guide may be or include concentric cutting guides.

Surgical methods of embodiments can further include mapping the vascular system on the facial anatomy of both the recipient and the donor and superimposing corresponding virtual representations of the vascular system and the facial anatomy onto the first 3D representation, such as shown in FIG. 4B

Surgical methods of embodiments can include a method for registration of a preoperative model, for example a model reconstructed from CT data, to donor and recipient anatomy. Such a method can include: creating a plurality of indentations on the donor skeleton, creating a plurality of virtual markers on the first 3D reconstruction of the donor skeleton corresponding to the locations of the indentations on the donor skeleton, placing a trackable object on at least one of the plurality of indentations, and determining whether a subsequent location of the virtual markers is within a predetermined tolerance relative to an actual subsequent location of the indentations.

EXAMPLES

Example 1

Figure 9A:
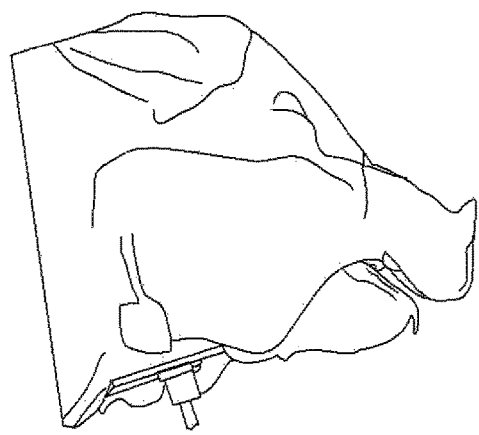
FIGS. 9A-9D schematically depict exemplary surgical results.
Figure 9B:
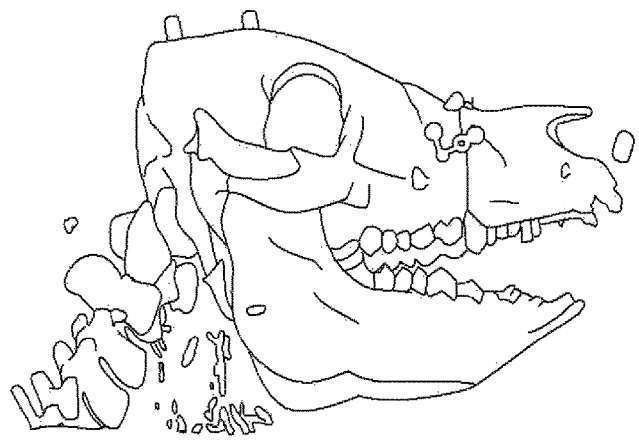
Figure 9C:
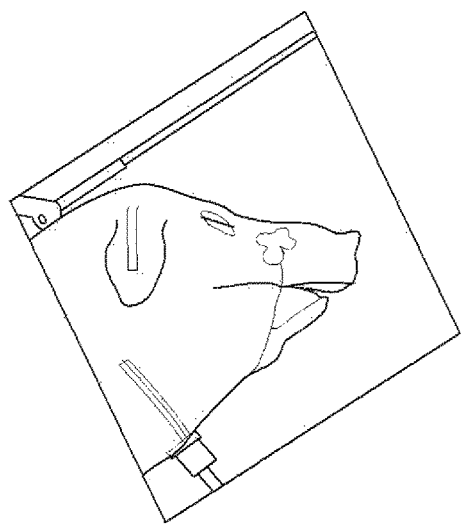
Figure 9D:
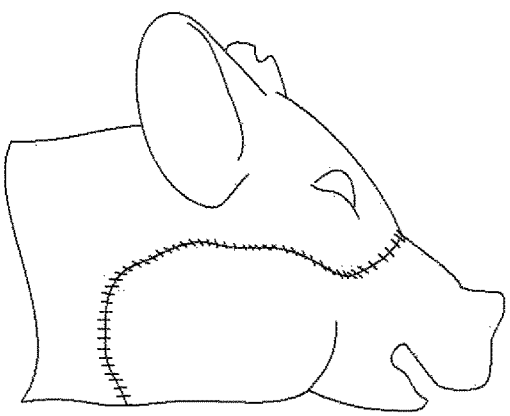

Live transplant surgeries (n=2) between four size-mismatched swine investigated whether or not an embodiment could actually assist a surgical team in planning and executing a desired surgical plan. As shown in FIGS. 9A-9B, the first live surgery confirmed the proposed utility of overcoming soft and hard tissue discrepancies related to function and aesthetics. The final occlusal plane within the first recipient was ideal and consistent with the virtual plan as seen on lateral cephalogram as shown in FIG. 10C. Pre-operative functional predictions of donor-to-recipient occlusion were realized based on cephalometric analyses as shown in FIG. 9C performed both before and after surgery. Soft tissue inconsistencies of the larger-to-smaller swine scenario were also reduced following the predicted movements of face, jaw and teeth as shown in FIG. 10D.

The second live surgery showed improved success as compared to its predecessor due to surgeon familiarity and technology modifications. System improvements and growing comfort of the surgeons led to reduced operative times for both donor and recipient surgeries. Overall the surgical time reduced from over 14 hours to less than 8 hours due to improved surgical workflow and increased comfort with a system of an embodiment.

Based on the results obtained in the live and plastic bone surgeries, the functions associated with setting up a system of an embodiment (attaching references, performing registration, attaching cutting guides) adds about 11 minutes to the total length of surgery.

Figure 11A:
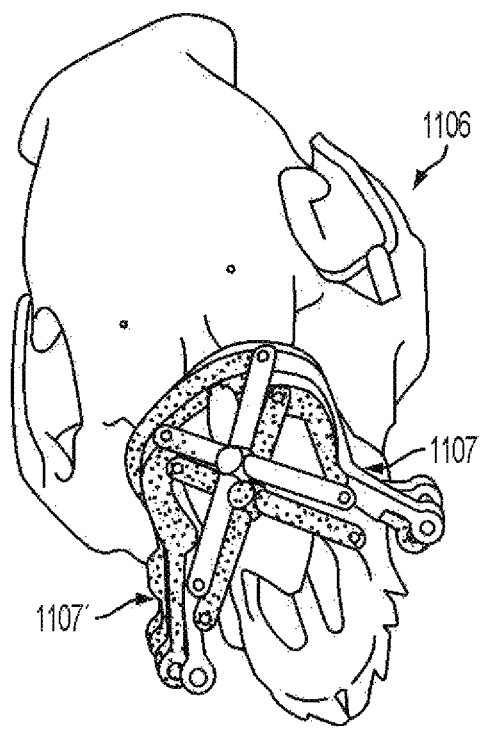
FIGS. 11A-11B are "on screen" images displayed by an imaging sub-system of a surgical system. The images depict an ideal location of a cutting guide versus an actual position and an actual inset position of a donor alloflap for aesthetic, dental, and skeletal relation in size-mismatched donors due to anterior translation of cutting guide.
Figure 11B:
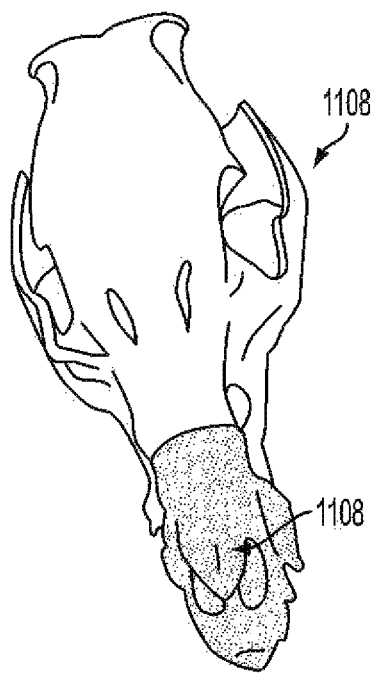
Figure 13A:
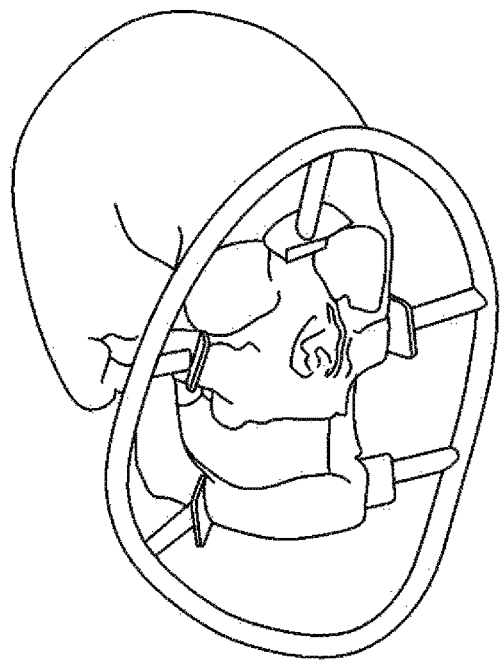
FIG. 13 shows a virtual placement of a cutting guide alongside photographs of an actual placement.
Figure 13B:
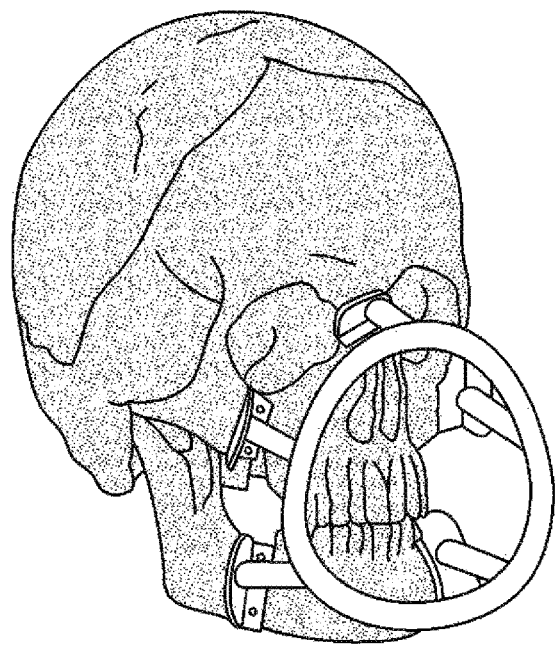
Figure 13C:
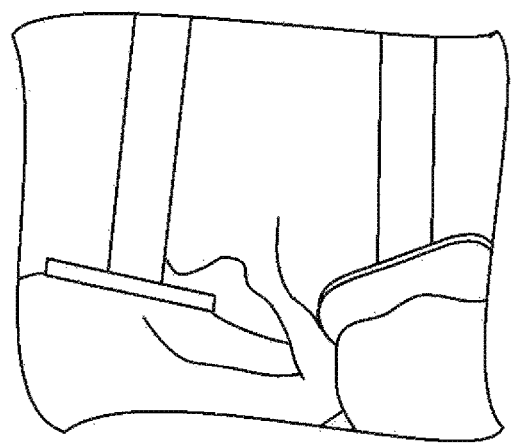
Figure 13D:
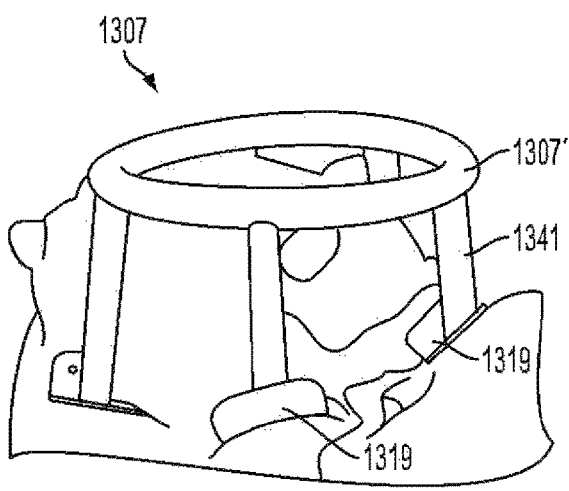

The system also recorded information, such as rendering information which can be stored in a storage medium of a workstation, relating the donor fragment 1002 to the recipient 1010 qualitatively as shown by color mismatch 1004, which matched the post-operative CT data as shown in FIG. 10. The recipient cutting guide 1107' was not placed as planned 1107 due to an unexpected collision between the cranial reference mount and the recipient cutting guide as shown in FIGS. 11A-11B. In this case, there was anterior translation of the cutting guide (toward the tip of the swine's snout) by approximately 4 cm.

Overall, the donor 1106 and recipient craniums (n=4) 1108 were registered successfully to the reference bodies for both live surgeries. The model to patient registration error across the surgeries was 0.6 (+/−0.24) mm. The cutting guide designs of the embodiments proved highly useful in carrying out the planned bone cuts, which compensated for size-mismatch discrepancies between donor and recipient. Marking spheres fixated to the guides allowed real-time movement tracking and "on-table" alloflap superimposition onto the recipient thereby allowing visualization of the final transplant result.

Example 2

Female and male donor heads (n=2), double-jaw, Le Fort III-based alloflaps were harvested using handheld osteotomes, a reciprocating saw, and a fine vibrating reciprocating saw. Both osteocutaneous alloflaps were harvested using a double-jaw, Le Fort III-based design (a craniomaxillofacial disjunction), with preservation of the pterygoid plates, incorporating all of the midfacial skeleton, complete anterior mandible with dentition, and overlying soft tissue components necessary for ideal reconstruction.

Prior to transplantation, both scenarios were completed virtually given the gender-specific challenges to allow custom guide fabrication as shown in panels A-H of FIG. 12. Once assimilated, the donor orthognathic two-jaw units were placed into external maxilla-mandibular fixation (MMF) using screw-fixated cutting guides to retain occlusal relationships during the mock transplants as shown in panels A-D of FIG. 13.

Figure 14A:
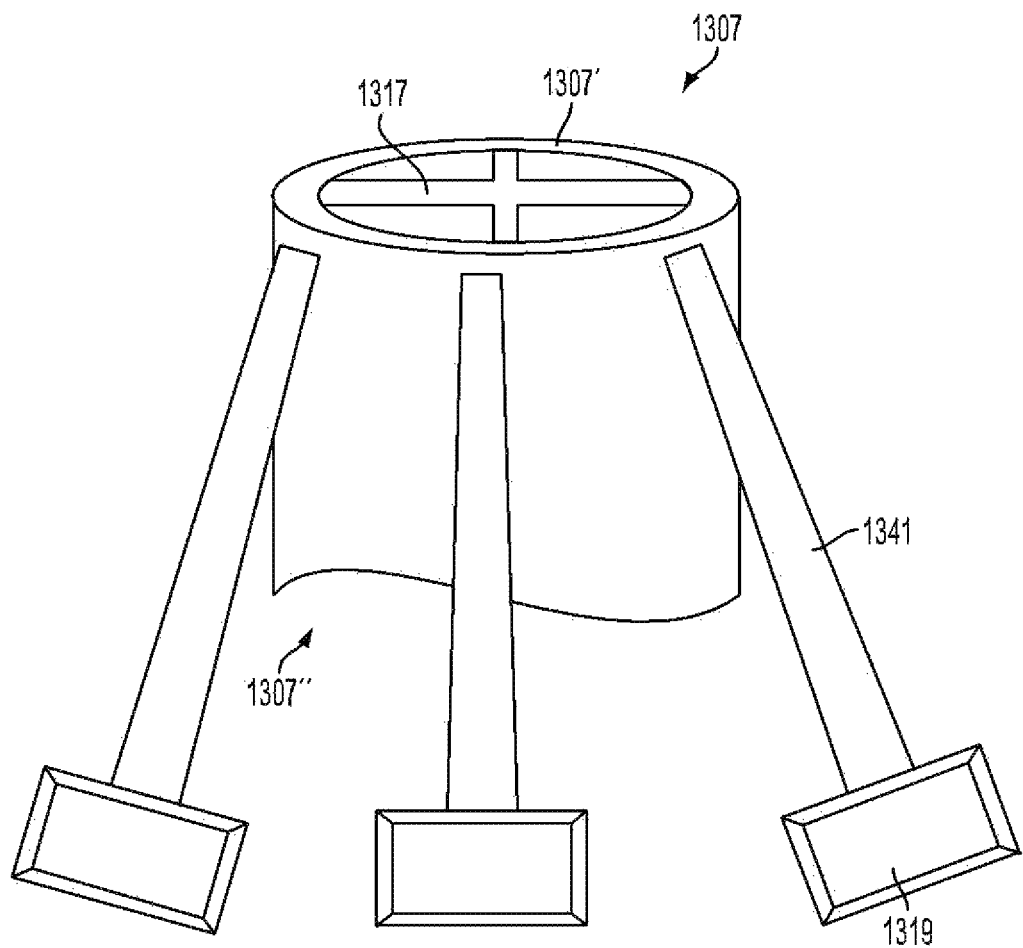
FIG. 14A illustrates a perspective view of a variation of a cutting guide, for example, a variation of the cutting guide of FIG. 13.
Figure 14B:
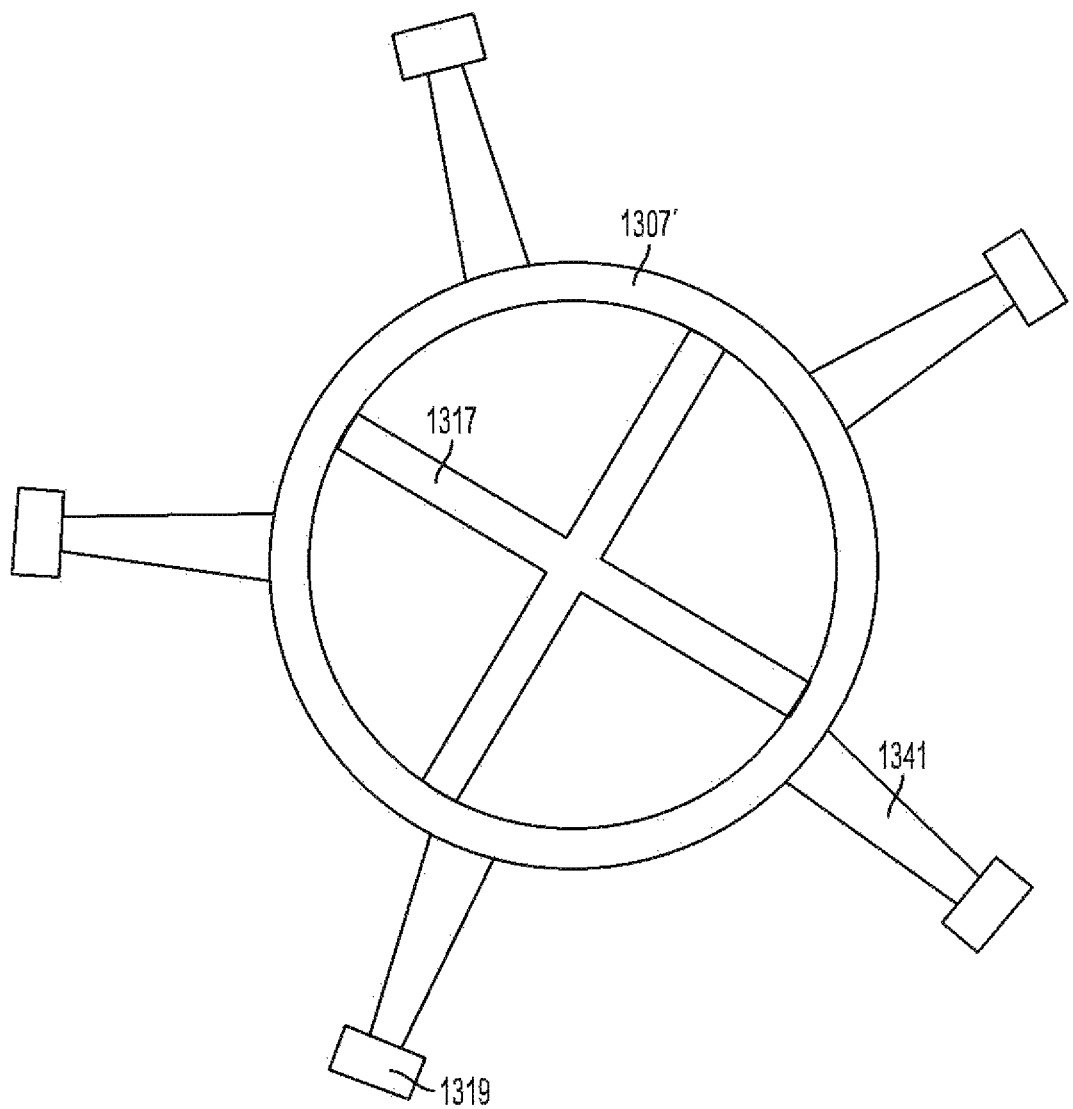
FIG. 14B illustrates a top view of a variation of a cutting guide, for example, a variation of the cutting guide of FIG. 13.

As shown in FIGS. 13, 14A-14B, an embodiment of a cutting guide 1307 can include a frame 1307' with at least one attachment surface 1319, for example 1 to 6 attachment surfaces, configured for attaching the cutting guide to a skeletal feature. The cutting guide can include a navigation surface 1317 (not shown in FIG. 13) connected to the frame. The navigation surface can include a reference geometry that can be tracked by a tracker, for example, via IR optical tracking. The at least one attachment surface 1319 can include a contoured surface corresponding to contours of portions of the skeletal feature, for example, such as the contours of a skeletal feature that intersect a planned-cut plane as indicated by 1319' in FIG. 12. The at least one attachment surface 1319 can be detachably connected to a skeletal feature. The at least one attachment surface 1319 can be detachably connected to an attachment guide 1341. The attachment guide 1341 can be detachably connected to a portion of the frame 1307'. For example, attachment guides 1341 can be detachably connected via slots integrated into frame 1307', or held in place against frame 1307 with screws or the like. In another embodiment, attachment guides 1341 are formed as portions of frame 1307' but can be removed. The frame can have a ring-like shape (as shown in FIG. 13) or can have a cylinder-like shape (as shown in FIG. 14A). Frame 1307' having a cylinder like shape can have a bottom surface 1307'' that rests against a patient's soft tissue to provide support for the frame.

For example, during a surgical procedure, 3D reconstructions of portions of a donor skeleton are created. Planned cutting planes are selected and a cutting guide with attachment surfaces having a contoured surface corresponding to contours of portions of the skeletal feature, for example, such as the contours of a skeletal feature that intersect a planned-cut plane, is designed. The designed cutting guide is manufactured via, for example, an additive manufacturing process. The designed cutting guide with an integrated navigation surface is attached to the patient. For example, the cutting guide can be designed such that it has a snap-on fit over the skeletal feature, which can be further secured to the skeletal feature with set screws. A surgeon removes a donor skeletal fragment with the cutting guide attached to the fragment. The donor skeletal fragment is then attached to the recipient. As the donor skeletal fragment is attached to the recipient, the attachment surfaces are removed from the donor fragment. For example, each of the attachment guides 1341 with a corresponding attachment surface 1319 can be detached from the frame 1307'. As this occurs, a cylindrical shaped frame 1307' has a bottom surface 1307'' that rests against the soft tissue of the patient to provide stability for the remaining portions of the cutting guide and to hold the navigation surface 1317' in place.

While the disclosure has been illustrated respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. For example, the embodiments described herein can be used for navigation and modeling for osteotomy guidance during double-jaw face transplantation, single-jaw maxillofacial transplantation, and any other neurosurgical, ENT/head and neck surgery, or oral maxillofacial surgical procedure alike.

Embodiments described herein can include platforms for preoperative planning and intraoperative predictions related to soft tissue-skeletal-dental alignment with real-time tracking of cutting guides for two mismatched jaws of varying width, height and projection. Additional safeguards, such as collection of confidence points, further enable intraoperative verification of the system accuracy. This, in addition to performing real-time plan verification via tracking and dynamic cephalometry, can considerably increase the robustness of the systems described herein. Moreover, systems of embodiments can include a modular system that allows additional functionality to be continually added.

Embodiments described herein can include an approach for resolving conflicts in case of position discrepancies between the placement of the guide and the guide position prompted by the navigation software. Such discrepancy may be due to either the guide (soft tissue interference, iatrogenic malpositioning, changes since the CT data was obtained or imperfections in cutting guide construction/printing), and/or the navigation system (e.g. registration error, or unintended movement of the kinematic markers). To resolve these source(s) of discrepancy, four indentations can be created on a bone fragment (confidence points) where a reference kinematic marker is attached. At any time during an operation, a surgeon can use a digitizer and compare the consistency of the reported coordinates of the indentations via navigation to their coordinates with respect to a virtual computer model.

Embodiments described herein can include a system that provides real-time dynamic cephalometrics and masticatory muscle biomechanical simulation for both planning and intraoperative guidance to ensure ideal outcomes in craniomaxillofacial surgery.

Additional Embodiments

Osseointegrated Dental Implants

Patients with poor or missing dentitions may require dental implants to improve mastication. A popular modality with increasing indications includes "osseointegrated dental implants". Oseeointegrated dental implants can include, and may consist of, a two-piece permanent implant device, which is placed into either the maxilla or mandible skeleton with a power drill for placement and stability. A second piece, in the shape of a tooth is screwed onto the secure base. An embodiment of the CAPE system described above can be used to provide the dentist or surgeon real-time cephalomteric feedback in an effort to restore ideal occlusion and predict optimized mastication with biomechanical predictions—as similar to maxillofacial transplantation. As such, the dentist or surgeon placing these items needs to know the bone stock quality of the jaw(s) and angle to place the framework.

Osseointegrated Craniofacial Prosthetics

Patients with severe cranial or facial disfigurement may be poor surgical candidates due to overwhelming co-morbities and/or because of an accompanying poor prognosis. Therefore, to help return these patients into society, some use craniofacial prosthetics as a way to restore "normalcy". Application of these three-dimensional prosthetics replacing absent craniofacial features (i.e., nose, eye, etc) may either be hand-molded/painted by an anaplastologist or printed with 3D technology by a prosthetician. Either way, in an embodiment, the CAPE system described above can provide a one-stop solution for patients requiring alloplastic and/or bioengineered prosthetic reconstruction for large craniomaxillofacial deformities. The craniofacial implants can be tracked as similar to a donor face-jaw-teeth segment described above. For example, pre-placement images of the prosthetic may be fabricated, and surgical plans may be optimized since these appliances are placed with osseointegrated devices as similar to dental implants described above—with rigid plates and screws. As such, the surgeon placing them needs to know the bone stock quality and angle to place the framework, and also needs to know with visual feedback as to the ideal position in three-dimensional space.

Craniomaxillofacial Trauma Reconstruction

Patients suffering from acute or chronic facial disfigurement are often seen by a craniomaxillofacial surgeon. Both penetrating and/or blunt trauma may cause significant damage to the underlying facial skeleton. As such, in an embodiment, the CAPE system technology described herein allows the surgeon to assess and optimize bone fragment reduction and reconstruction with real-time feedback. In addition, fractures affecting the jaws can be aided by real-time cephalometrics in hopes to restore the patient back to their pre-trauma angle/measurements (as a way to assure proper occlusion). Navigation, as described above in an embodiment of the CAPE system, can be exceptionally helpful for orbit fractures around the eye or cranial fractures around the brain, since the nerve anatomy is delicate and consistent—which makes it applicable to the CAPE system. In summary, a surgeon (including the likes of a Plastic surgeon, ENT surgeon, oral/OMFS surgeon, oculoplastic surgeon, neurosurgeon) reducing craniofacial fractures needs to know the bone stock quality remaining, where plates/screws are best placed, and the optimal plan prior to entering the operating room.

Neurosurgical Procedures

Neurosurgeons frequently perform delicate craniotomies for access for brain surgery. Currently, there are several navigational systems available. However, none of the conventional systems include features described in the embodiments of the CAPE platform as described above. That is, the conventional systems lack the ability to assist both preoperatively with planning AND with intra-operative navigation for execution assistance. In addition, the current neurosurgery systems require the head to be placed in antiquated "bilateral skull clamp pins" prior to starting surgery. This means that before each neurosurgery procedure starts, a big 3-piece clamp is crunched onto the skull of the patient to make sure the head does not move during surgery, particularly to allow for use of the conventional navigation systems. However, embodiments of the CAPE system, such as those described above, use a small, modified rigid cranial reference mount which removes the need for using a big, bulky clamp from the field and allows the surgeon to rotate the patient's head if and when needed. To a craniofacial plastic surgeon, who often is consulted to assist with scalp reconstruction, elimination/removal of such pins from the surgical field is a huge advantage. For example, elimination of the pins makes scalp reconstruction in the setting of neurosurgery much safer since the pins aren't present to hold back mobilization and dissection of the nearby scalp, which is needed often for complex closure. It also, reduces the risk of surgical contamination since the current setup with pins is bulky and makes surgical draping and sterility much more difficult and awkward. A small cranial mount as part of the CAPE system is a huge advancement for the field.

Congenital Deformity Correction

Unfortunately, newborns are commonly born with craniofacial deformities to either maternal exposure or genetic abnormalities. As such, they may have major development problems with their skeleton and the overlying structures (eyes, ears, nose) may therefore appear abnormal. In addition, newborns may suffer from craniosynostosis (premature fusing of their cranial sutures) which causes major shifts in the shape of their head at birth. In an embodiment, the CAPE system described above, can be utilized to address such congenital deformities, irrespective of etiology. For example, if a 16 year old needs to have major Le Fort surgery to move the central facial skeleton into better position forward to improve breathing, mastication, and appearance, use of the CAPE system technology for both pre- and intra-operatively provides a huge advancement for the field.

Head/Neck and Facial Reconstruction (ENT Surgery)

Head and neck surgeons in the specialty of Otolarygology (ENT) are frequently reconstructing facial skeletons. Reasons include post-tumor resection, facial trauma, aesthetic improvement, congenital causes and/or functional improvement (nose, mouth, eyes, etc). Therefore, this specialty would greatly benefit from use of the CAPE system technology described herein. For example, in an embodiment, use of the CAPE system can be used in a wide range of surgeries including such instances as post-trauma fracture reduction/fixation, free tissue transfer planning and execution (i.e., free flap reconstruction with microsurgical fibula flaps for large bone defects where the leg bone receives dental implants for jaw reconstruction), smaller jaw reconstruction cases with implant materials, and/or anterior skull base reconstructions with neurosurgery following tumor resection. This specialty is very diverse, and therefore the CAPE system's easy adaptability can help make it greatly valuable to this group of surgeons.

Orthognathic Surgery

Orthognathic surgery describes any of surgical procedure type moving the jaw and/or jaw-teeth segments. This is most commonly performed by either oral surgeons, oral-maxillofacial surgeons (OMFS), or plastic surgeons. It is done currently both in the hospital as an insurance case or in the outpatient setting for a fee-for-service. It may be indicated for enhanced mastication, improved aesthetics, and/or both reasons. Having the ability to plan and predict jaw movements based on biomechanical muscle (i.e., external) forces will be immensely valuable to this field. In an embodiment, surgeons can utilize the CAPE system described above to predict functional jaw movements both at time of surgery and after surgery (1, 5, 10, 20 years post-op). In addition, in an embodiment, a surgeon can utilize the CAPE system to provide real-time cephalometric feedback, which provides an advancement not seen in the conventional systems. In comparison, for the last several centuries, oral surgeons have used splints fabricated in the dental lab pre-operatively for assistance in the operating room to help confirm dental alignment as planned. This takes time (e.g., 4-6 hours to make by hand), effort, and money. In contrast to the conventional systems, surgeons utilizing the CAPE system can go to the operating room with pre-fabricated cutting guides and tracking instruments, cut the jaws where planned, and then match the teeth on the table based on real-time cepholmetric feedback and biomechanical jaw simulation to predict post-operative mastication—unlike ever before. For example, use of the CAPE system will allow surgeons to know instantaneously if the aesthetic and functional angles/measurements are ideal and where they should be. In addition, the CAPE system is able to supply palatal cutting guides and pre-bent metal fixation plates (as opposed to the conventional methods that require handbending each plate for proper shape). In summary, the CAPE system will be a "game-changer" for orthognathic surgery.

"Computer-Assisted Cranioplasty"

This application aims at improving immediate surgical repair of large cranial defects (>5 cm$^2$) with customized craniofacial implants following benign/malignant skull neoplasm (tumor) resection (i.e., referred to as "single-stage implant cranioplasty"). Currently, it is challenging to reconstruct these patients with pre-fabricated implants since the actual size/shape is unknown until the tumor is removed. We therefore envision using our novel computer-assisted surgical workstation to significantly reduce the intraoperative time used for reshaping/resizing the customized implant. The workstation will provide visualization related to the tumor, the resulting skull defect, and the reshaped implant for exact positioning. This development will build upon this Computer-Assisted Planning and Execution (CAPE) system for Le Fort-based, Face-Jaw-Teeth transplantation and will help to improve both the pre-operative planning and intra-operative execution of single-stage implant cranioplasties. Cranioplasties are performed to reconstruct large defects following stroke, trauma, aneurysmal bleeding, bone flap removal for infection, and oncological ablation. However, oncological defects are commonly reconstructed with "off-the-shelf" materials, as opposed to using a pre-fabricated customized implant—simply because the exact defect size/shape is unknown. With this in mind, this disclosure provides the surgeon with a computer-assisted algorithm to allow him/her to reconstruct tumor defects with pre-customized cranial implants (CCIs) for an ideal result.

Nearly 250,000 primary brain tumors/skull-based neoplasms are diagnosed each year resulting in a range of 4500-5000 second-stage implant cranioplasties/year. Unfortunately, the common tumor defect cranioplasty is reconstructed with on-table manipulation of titanium mesh, liquid polymethylmethacrylate (PMMA), liquid hydroxyapatitie/bone cement (HA) or autologous split-thickness calvarial bone grafts, which forces the surgeon to shape/mold these materials to an approximate size/shape. This results in some form of craniofacial asymmetry and a post-operative appearance which is suboptimal. Furthermore, the difficult shaping process may take several hours—which in turn increases anesthesia, total blood loss, risk for infection, morbidity, and all costs associated with longer operative times. Therefore, there is significant opportunity to extend this CAPE to thousands of patients.

In 2002, the advent of computer-aided design and manufacturing (CAD/CAM) was used for the first time to pre-emptively match the contralateral, non-operated skull for ideal contour and appearance—and thus the CCI was born. However, cranioplasties with these "perfect" implants can only be performed as "second stage" operations—to ensure that the CCI fits perfectly into the skull defect. In recent years, there have been several reports demonstrating the feasibility of CCIs for "single-stage cranioplasty"—by using a handheld bur to shave down the implant artistically. Although limited, the authors report acceptable outcomes, a trend towards decreased operative times, and less overall surgery required (i.e., one stage instead of two). The main challenges are limitations in both assessing and predicting each tumor-resection deformity pre-surgery. This thereby limits the applicability of CCIs in this patient population. Various barriers include 1) unknown exact tumor size, 2) unknown growth from time of pre-op CT scan-to-actual day of surgery, and 3) the unknown resection margins needed to minimize local recurrence. For these cases, the CCI would need to be reshaped/resized intraoperatively from a size slightly larger than expected—which is a process that may take several (2-4) hours. However, there are currently no established planning and execution systems available to assist these single-stage reconstructions. Therefore, this Computer-Assisted Planning and Execution (CAPE) system will assist surgeons in performing single-stage cranioplasty following oncological resection. This disclosure covers the entire CAPE system, which is a single, seamless platform capable of both planning (pre-op use) and navigation (intra-op use)—distinctly different than all other current systems that do either one or the other (see Table 2 below). In addition, its hardware such as trackable cutting guides and rigid cranial reference mount (described herein) are each uniquely valuable. The CAPE architecture will provide reconstructive surgeons all of the necessary algorithms for real-time updates related to single-stage customized implant cranioplasty.

TABLE 2

| | Innovation Group | Brainlab | Med Surg Services | Medtronic | Pacific | Fraxim/ Ortho Surg | Siemens | Smith & Nephew | Stryker | Zimmer | CAPE |
|---|---|---|---|---|---|---|---|---|---|---|---|
| Comparison of CAPE and Competitive Solutions. | | | | | | | | | | | |
| Virtual Planning | ✓ | X | ✓ | X | X | X | X | X | X | X | ✓ |
| Navigation | ✓ | ✓ | ✓ | ✓ | ✓ | ✓ | ✓ | ✓ | ✓ | ✓ | ✓ |
| Real time cephalometrics | X | X | X | X | X | X | X | X | X | X | ✓ |

TABLE 2-continued

Comparison of CAPE and Competitive Solutions.

|  | Innovation Group | Brainlab | Med Surg Services | Medtronic | Pacific | Fraxim/ Ortho Surg | Siemens | Smith & Nephew | Stryker | Zimmer | CAPE |
|---|---|---|---|---|---|---|---|---|---|---|---|
| Trackable cutting guides | X | X | X | X | X | X | X | X | X | X | ✓ |
| Biomechanical Simulation | X | X | X | X | X | X | X | X | X | X | ✓ |
| Multiple stations | X | X | X | X | X | X | X | X | X | X | ✓ |

Figure 15:
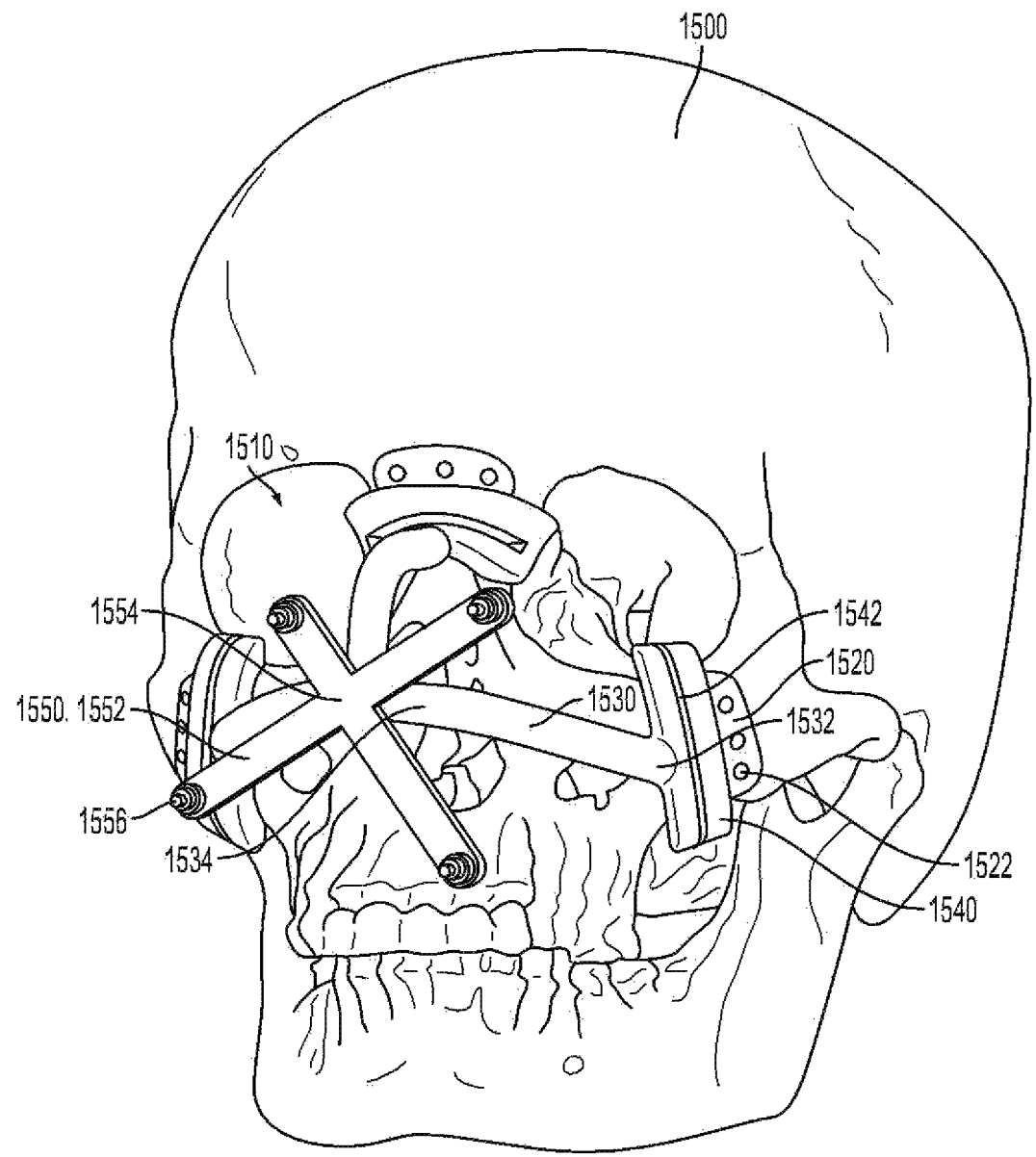
FIG. 15 illustrates an illustrative surgical guide assembly coupled to a skull.

FIG. 15 illustrates an illustrative surgical guide assembly 1510 coupled to a skull 1500. The guide assembly 1510 may include one or more attachment devices 1520 (three are shown) for coupling the guide assembly 1510 to the skull 1500. As shown, the attachment devices 1520 are configured to be coupled to the left zygomatic bone, the right zygomatic bone, and the nasal bone of the skull 1500. In other embodiments, the attachment devices 1520 may be configured to be coupled to other portions of the skull 1500, such as the maxilla, mandible, or a combination thereof. In yet other embodiments, the attachment devices 1520 may be configured to be coupled to bones other than the skull.

The attachment devices 1520 may each include one or more openings 1522 (three are shown) formed therethrough. A screw, bolt, or the like (not shown in FIG. 15) may be inserted through each opening 1522 and at least partially into the skull 1500 to couple the guide assembly 1510 to the skull 1500. For example the screws may be from about 1 mm to about 3 mm surgical screws or from about 1.5 mm to about 2.5 mm surgical screws. Although shown as including openings 1522 configured to receive screws, in other embodiments, the attachment devices 1520 may include other mechanical connections to the skull 1500, such as clamps or an adhesive.

The guide assembly 1510 may also include one or more arms 1530 (three are shown). A first end 1532 of each arm 1530 may be coupled to or integral with one of the attachment devices 1520. In at least one embodiment, a second end 1534 of each arm 1530 may be coupled to or integral with a common point. For example, as shown, the second ends 1534 of the arms 1530 may be coupled to one another. As shown, the arms 1530 may be curved or bent such that the second ends 1534 are positioned farther out from the skull 1500 than the first ends 1532. In other embodiments, the arms 1530 may be substantially straight.

The guide assembly 1510 may further include one or more cut location indicators 1540 (three are shown). As shown in FIG. 15, the cut location indicators 1540 may be positioned between the attachment devices 1520 and the first ends 1532 of the arms 1530. As later shown, in other embodiments, the attachment devices 1520 may be positioned between the first ends 1532 of the arms 1530 and the cut location indicators 1540.

The cut location indicators 1540 may identify locations on the skull 1500 where the surgeon should make the cuts. In at least one embodiment, the cut location indicators 1540 may include recesses 1542 that extend partially through the guide assembly 1510. In another embodiment, the cut location indicators 1540 may be or include slots that extend all the way through the guide assembly 1510 providing a path for a cutting device (e.g., a saw) to pass therethrough to the skull 1510.

A support structure 1550 may be coupled to or integral with the guide assembly 1510. For example, the support structure 1550 may be coupled to or integral with the arms 1530 (e.g., proximate to the second ends 1534 of the arms 1530). The support structure 1550 may be or include one or more rods 1552 (four are shown). The rods 1552 may be coupled to or integral with one another at a common point 1554 (e.g., proximate to where the rods 1552 connect to the arms 1530). As shown, the rods 1552 may be substantially straight and in the same plane. In other embodiments, the rods 1552 may be curved or bent.

An angle between two adjacent rods 1552 may be from about 5° to about 175°, about 20° to about 160°, about 45° to about 135°, or about 60° to about 120°. As shown, the angles between adjacent rods 1552 are about 90°. The rods 1552 may each be substantially the same length, or two or more rods 1552 may be different lengths, as measured from the common point 1554.

An end of each rod 1552 may include a connector 1556. As shown, the connectors 1556 may be male connectors that extend away from the ends of the rods 1552 and/or away from the skull 1550. In another embodiment, the connectors 1556 may be female connectors (e.g., a threaded recess or opening). As discussed in greater detail below, a trackable feature may be coupled to each connector 1556.

The attachment devices 1520, the arms 1530, the cut location indicators 1540, the support structure 1550, or a combination thereof may be made from a polymer, a resin, an epoxy, or a combination thereof. In addition, the attachment devices 1520, the arms 1530, the cut location indicators 1540, the support structure 1550, or a combination thereof may be integral with one another and manufactured by a 3D printer.

Figure 16:
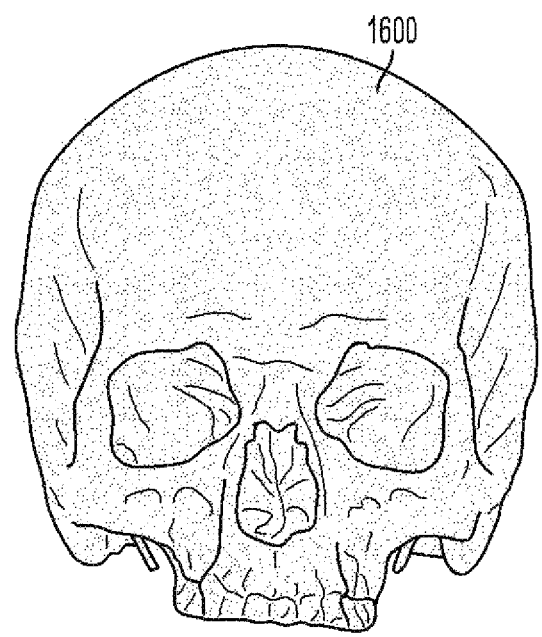
FIGS. 16 and 17 illustrate 3D scans of a donor skull and a recipient skull, respectively.
Figure 17:
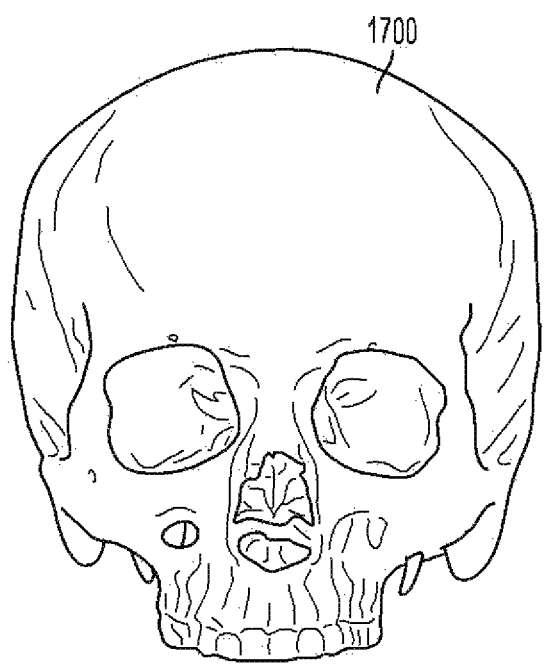

FIGS. 16-30 illustrate a method for performing craniomaxillofacial surgery using the guide assembly 1510. More particularly, FIGS. 16 and 17 illustrate 3D scans of a donor skull 1600 and a recipient skull 1700, respectively. The donor skull 1600 may be selected to be similar in size and shape to the recipient skull 1700. The similarity may be determined by comparing one or more scans. The scans may be 3D images of the skulls 1600, 1700 that are reconstructions of CT scans. Although two human skulls 1600, 1700 are shown, it will be appreciated that the following method and guide assembly 1500 may be applied to other bones and/or other species.

Figure 18:
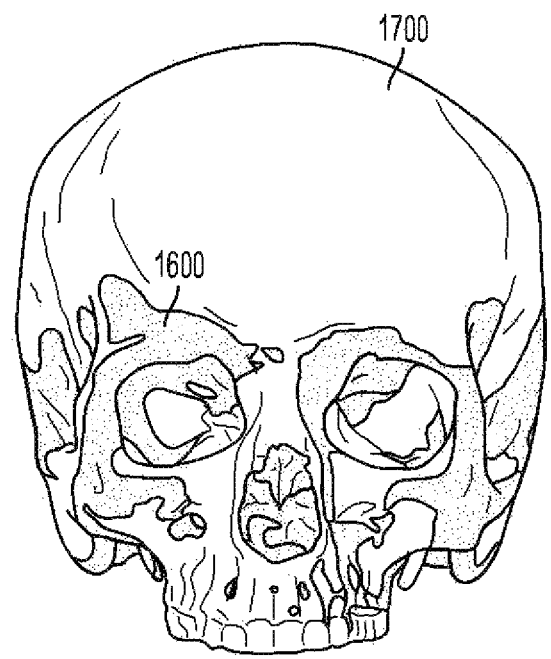
FIG. 18 illustrates a scan of the donor and recipient skulls aligned in the same space such that they at least partially overlap one another.

FIG. 18 illustrates the images of the donor and recipient skulls 1600, 1700 aligned in the same space such that they at least partially overlap one another. As shown, the skulls 1600, 1700 are a close match, but are not identical. The shading illustrates where the donor skull 1600 extends beyond the recipient skull 1700.

Figure 19:
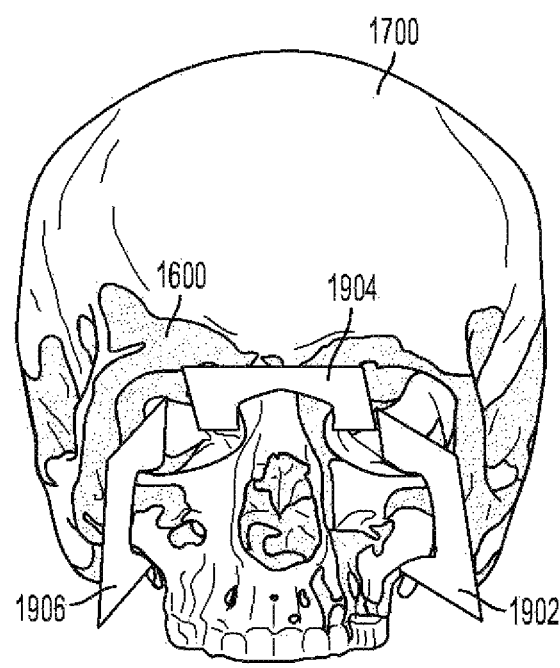
FIG. 19 illustrates cutting planes identified through the aligned donor and recipient skulls shown in FIG. 18.

FIG. 19 illustrates cutting planes (three are shown: 1900, 1902, 1904) identified through the images of the aligned donor and recipient skulls 1600, 1700 shown in FIG. 18. Once the skulls 1600, 1700 are aligned, one or more cutting planes 1900, 1902, 1904 may be selected with respect to the skulls 1600, 1700. As shown, the cutting planes 1900, 1902, 1904 extend through the left zygomatic bone, the right zygomatic bone, and the nasal bone, respectively. However, in other embodiments, the cutting planes 1900, 1902, 1904 may extend through other bones in the skulls 1600, 1700 or other bones in the body.

Figure 20:
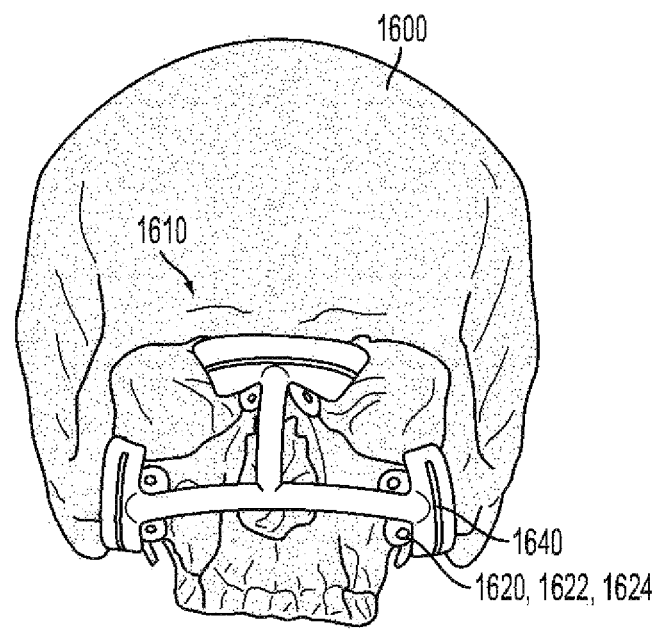
FIGS. 20 and 21 illustrate guide assemblies coupled to the donor and recipient skulls, respectively.
Figure 21:
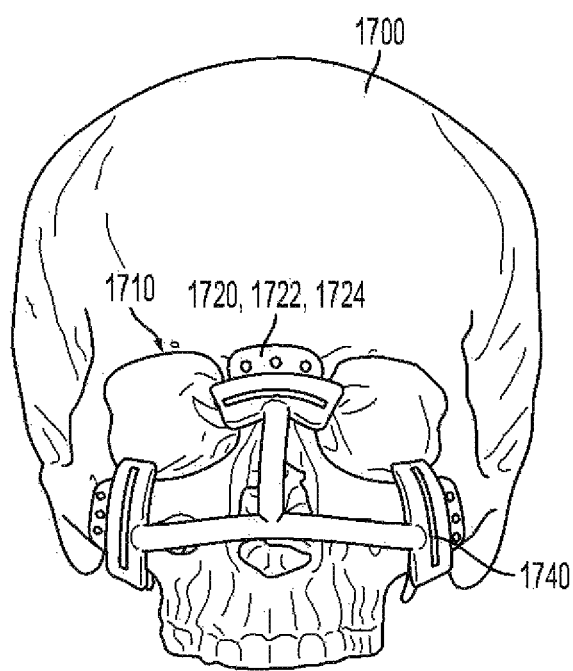

FIGS. 20 and 21 illustrate guide assemblies 1610, 1710 coupled to the donor and recipient skulls 1600, 1700, respectively. The guide assemblies 1610, 1710 may be similar to the guide assembly 1510 described above with respect to FIG. 15. As shown in FIG. 20, the first guide assembly 1610 may be aligned with the donor skull 1600. More particularly, the cut location indicators 1640 in the first guide assembly 1610 may be aligned with the cutting planes 1900, 1902, 1904 through the donor skull 1600 (as shown in FIG. 19). Once aligned, the attachment devices 1620 may be coupled to the donor skull 1600. For example, a plurality of screws 1624 may be inserted through the openings 1622 in the attachment devices 1620 and at least partially into the donor skull 1600. This may secure the first guide assembly 1610 to the donor skull 1600. The attachment devices 1620 may be positioned inward from the cut location indicators 1640 on the first guide assembly 1610. As such, the attachment devices 1640 may be coupled to the portion of the donor skull 1600 to be removed.

Similarly, as shown in FIG. 21, a second guide assembly 1710 may be aligned with the recipient skull 1700. More particularly, the cut location indicators 1740 in the second guide assembly 1710 may be aligned with the cutting planes 1900, 1902, 1904 through the recipient skull 1700 (as shown in FIG. 19). Once aligned, the attachment devices 1720 may be coupled to the recipient skull 1700. For example, a plurality of screws 1724 may be inserted through the openings 1722 in the attachment devices 1720 and at least partially into the recipient skull 1700. This may secure the second guide assembly 1710 to the recipient skull 1700. The attachment devices 1720 may be positioned outward from the cut location indicators 1740 on the second guide assembly 1710. As such, the attachment devices 1720 may be coupled to the remainder of the recipient skull 1700 (i.e., not the portion to be removed).

Figure 22:
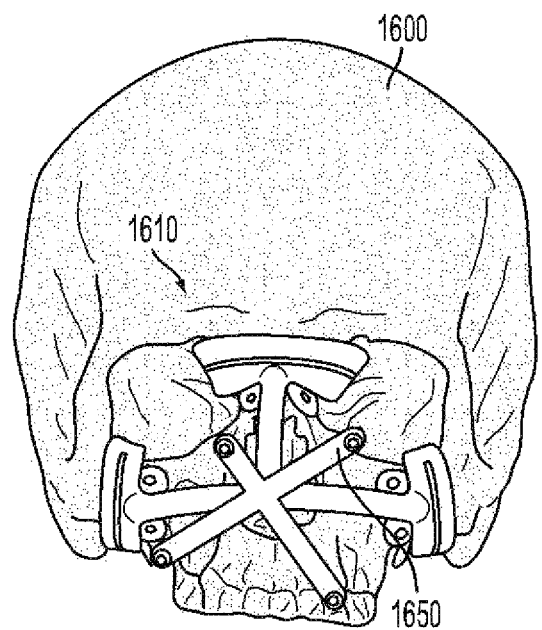
FIGS. 22 and 23 illustrate support structures coupled to the guide assemblies on the donor and recipient skulls, respectively.
Figure 23:
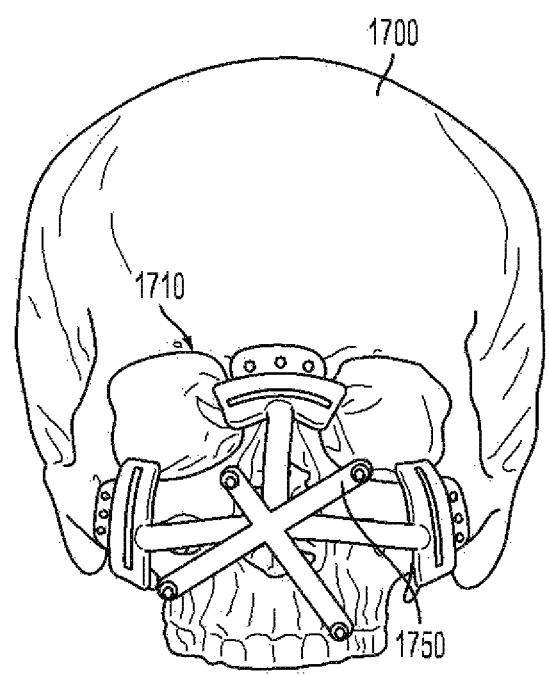

FIGS. 22 and 23 illustrate support structures 1650, 1750 coupled to the guide assemblies 1610, 1710 on the donor and recipient skulls 1600, 1700, respectively. The support structures 1650, 1750 may be coupled to the first and second guide assemblies 1610, 1710 either before or after the guide assemblies 1610, 1710 are coupled to the skulls 1600, 1700. The support structures 1650, 1750 may be in substantially the same position and/or orientation with respect to the skulls 1600, 1700.

Figure 24:
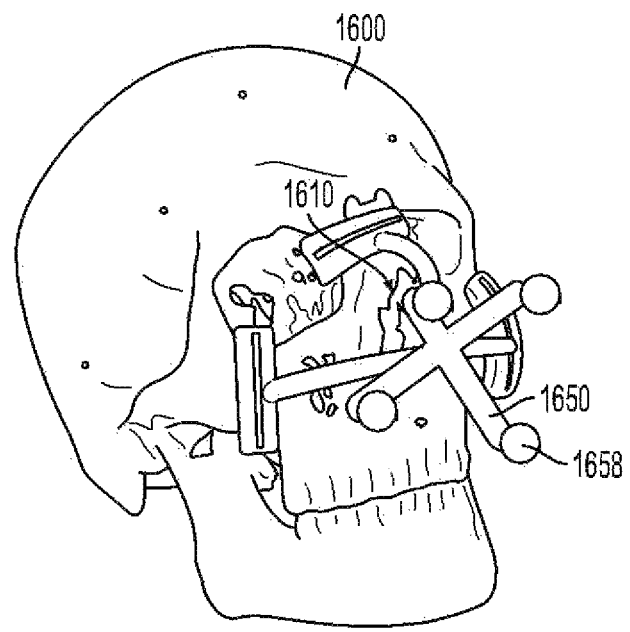
FIGS. 24 and 25 illustrate trackable features coupled to the support structures on the donor and recipient skulls, respectively.
Figure 25:
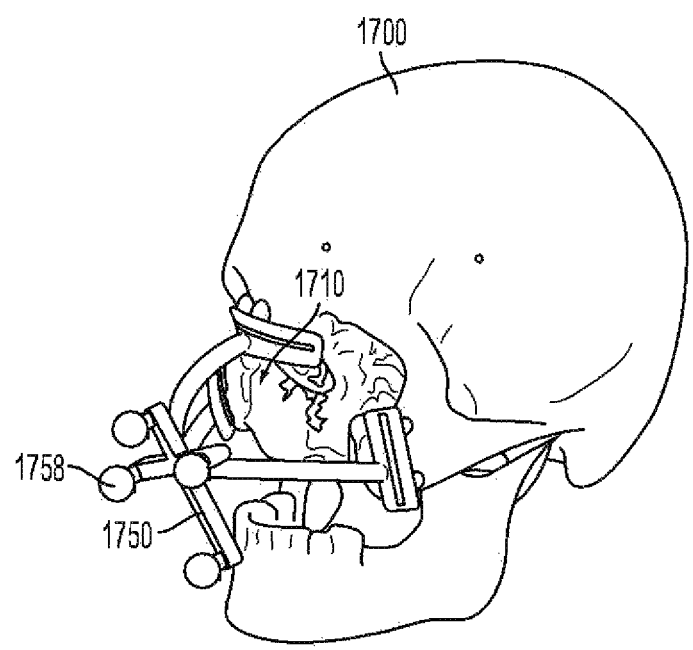

FIGS. 24 and 25 illustrate trackable features 1658, 1758 coupled to the support structures 1650, 1750 on the donor and recipient skulls 1600, 1750, respectively. One or more trackable features 1658, 1758 may be coupled to each of the support structures 1650, 1750. As shown, four trackable features 1658, 1758 are coupled to each of the support structures 1650, 1750; however, in other embodiments, more or fewer trackable features may be used. The trackable features 1658, 1758 may be coupled to the connectors on the support structures 1650, 1750 (e.g., via a threaded connection). The trackable features 1658, 1758 may be in substantially the same position and/or orientation with respect to the skulls 1600, 1700. The trackable features 1658, 1758 may be optical trackable features such as reflective spheres.

Figure 26:
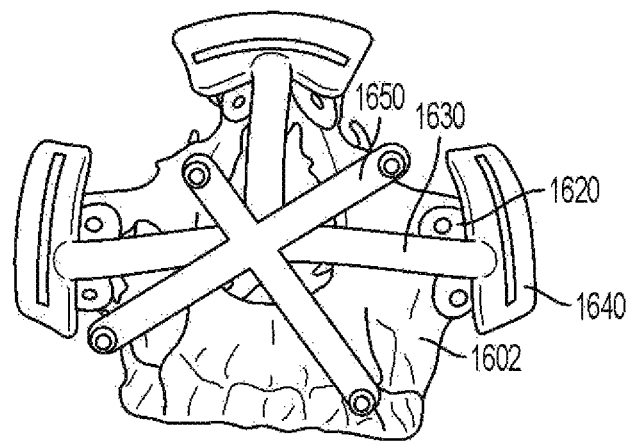
FIG. 26 illustrates a portion of the donor skull after being removed from the remainder of the donor skull.
Figure 27:
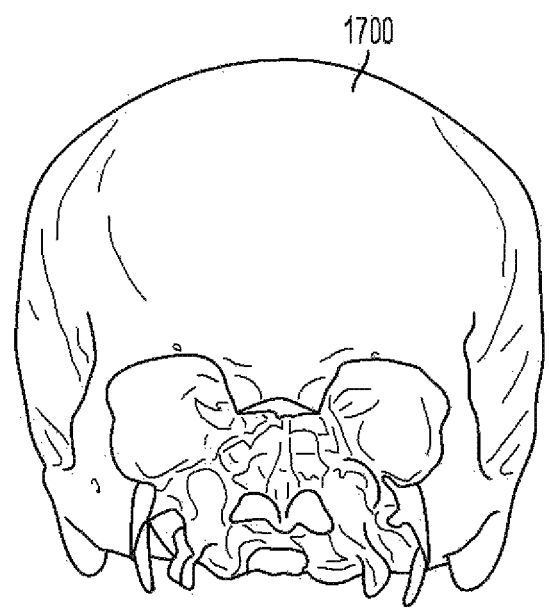
FIG. 27 illustrates the recipient skull after a corresponding portion of the recipient skull has been removed.

FIG. 26 illustrates a portion 1602 of the donor skull 1600 after being removed from the remainder of the donor skull 1600, and FIG. 27 illustrates the recipient skull 1700 after a corresponding portion of the recipient skull 1700 has been removed. Once the guide assemblies 1610, 1710 are coupled to the skulls 1600, 1700, the surgeon (or two different surgeons) may remove corresponding portions 1602 from each skull 1600, 1700. For example, looking at the donor skull 1600, the surgeon may use a saw to cut along the path identified by the cut location indicators 1640 to free the portion 1602 from the remainder of the skull 1600.

Figure 28:
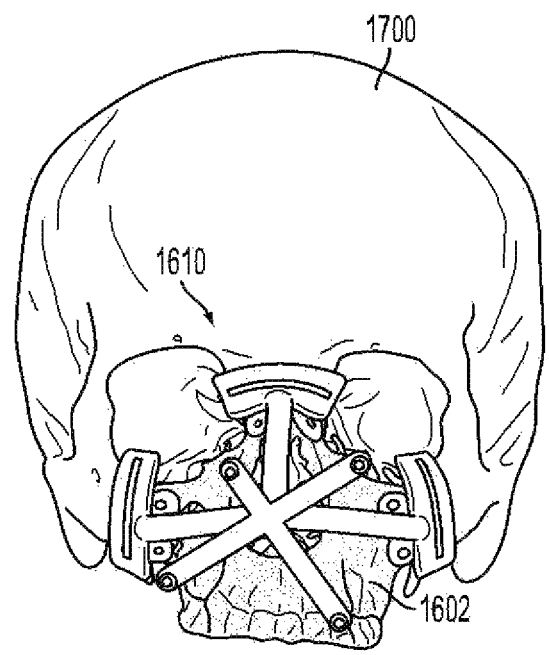
FIG. 28 illustrates the portion of the donor skull being aligned with the recipient skull before the guide assembly is removed.
Figure 29:
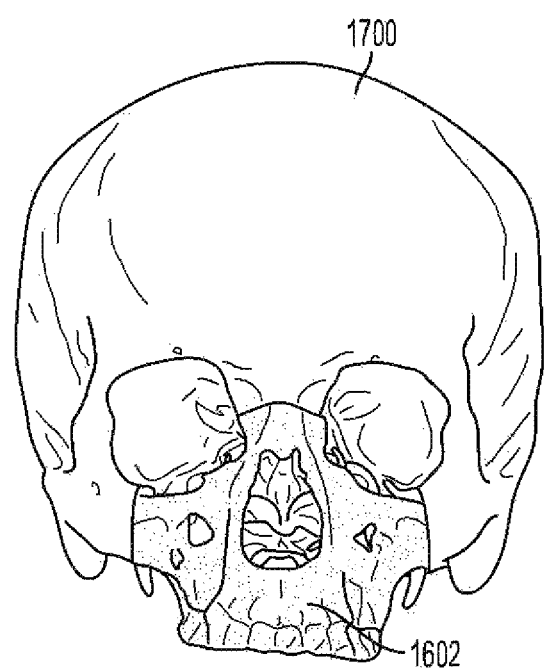
FIG. 29 illustrates the portion of the donor skull aligned with the recipient skull after the guide assembly is removed.

FIG. 28 illustrates the portion 1602 of the donor skull 1600 being aligned with the remainder of the recipient skull 1700 before the guide assembly 1610 is removed. FIG. 29 illustrates the portion 1602 of the donor skull 1600 aligned with the recipient skull 1700 after the guide assembly 1650 is removed. In at least one embodiment, the guide assembly 1610 may remain coupled to the portion 1602 of the donor skull 1600 as the portion 1602 of the donor skull 1600 is aligned with the remainder of the recipient skull 1700. Once aligned, the guide assembly 1610 may be removed from the portion 1602 of the donor skull 1600 (e.g., by removing the screws 1624 in the attachment devices 1620).

Figure 30:
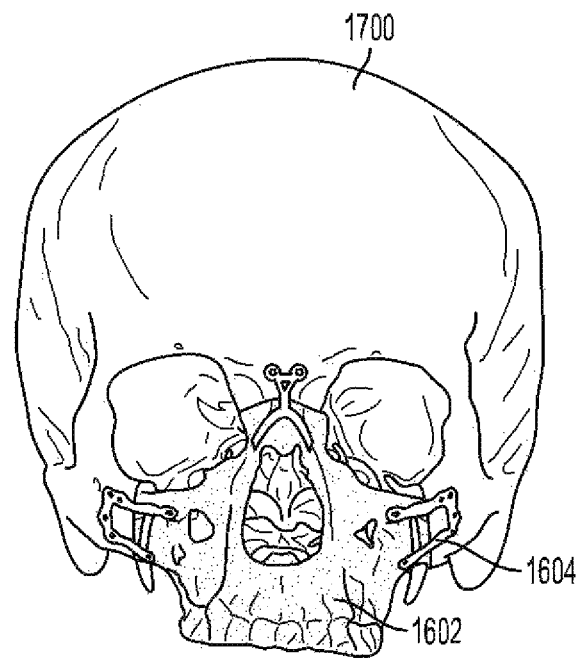
FIG. 30 illustrates the portion of the donor skull coupled to the recipient skull.

FIG. 30 illustrates the portion 1602 of the donor skull 1600 coupled to the recipient skull 1700. With the guide assembly 1610 out of the way, the portion 1602 of the donor skull 1600 may be coupled to the remainder of the recipient skull 1700. This may be accomplished by using one or more maxillofacial fixation plates 1604.

The terms "couple," "coupled," "connect," "connection," "connected," "in connection with," and "connecting" refer to "in direct connection with" or "in connection with via one or more intermediate elements or members." Furthermore, to the extent that the terms "including", "includes", "having", "has", "with", or variants thereof are used in either the detailed description and the claims, such terms are intended to be inclusive in a manner similar to the term "comprising." As used herein, the phrase "one or more of", for example, A, B, and C means any of the following: either A, B, or C alone; or combinations of two, such as A and B, B and C, and A and C; or combinations of three A, B and C.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A surgical guide assembly for craniomaxillofacial surgery, comprising:
   an implant surgical guide assembly, comprising
      at least one attachment device configured to be coupled to a craniomaxillofacial implant;
      a trackable feature coupled to the at least one attachment device of the implant surgical guide assembly; and
      a tracker dynamically tracking the trackable feature of the implant surgical guide assembly in three-dimensional space to provide intraoperative positioning feedback;
   a recipient surgical guide assembly, comprising
      at least one attachment device configured to be coupled to a bone of a craniomaxillofacial skeleton of the recipient;
      a cut location indicator coupled to the at least one attachment device, wherein the cut location indicator is configured to identify a location where the recipient bone is to be cut;
      a trackable feature coupled to the at least one attachment device; and a tracker dynamically tracking the trackable feature of the recipient surgical guide assembly and the trackable feature of the implant surgical guide assembly to provide intraoperative positioning feedback.

2. The surgical guide assembly according to claim 1, further including a communication link between the recipient surgical guide assembly and the implant surgical guide assembly.

3. The surgical guide assembly according to claim 2, wherein the recipient surgical guide assembly includes a computer work-station and the implant surgical guide assembly includes a computer work-station.

4. The surgical guide assembly according to claim 2, wherein the recipient surgical guide assembly includes a computer work-station.

5. The surgical guide assembly according to claim 1, wherein the recipient surgical guide assembly includes a computer work-station and the implant surgical guide assembly includes a computer work-station.

6. The surgical guide assembly according to claim 1, wherein the recipient surgical guide assembly and the implant surgical guide assembly provide real-time feedback.

7. The surgical guide assembly according to claim of claim 1, wherein the trackable feature of the implant surgical guide assembly is a reflective sphere and the trackable feature of the recipient surgical guide assembly is a reflective sphere.

8. The surgical guide assembly according to claim of claim 1, wherein the craniomaxillofacial implant is a donor implant, a dental implant, or a craniofacial prosthetic.

9. The surgical guide assembly according to claim of claim 1, wherein the attachment device of the implant surgical guide assembly, the attachment device of the recipient surgical guide assembly, and the cut location indicator are made from a polymer, a resin, an epoxy, or a combination thereof.

10. The surgical guide assembly according to claim of claim 1, wherein the at least one attachment device of the implant surgical guide assembly includes a plurality of attachment devices and the at least one attachment device of the recipient surgical guide assembly includes a plurality of attachment devices.

\* \* \* \* \*